US009801372B2

(12) United States Patent
Ishaque et al.

(10) Patent No.: US 9,801,372 B2
(45) Date of Patent: Oct. 31, 2017

(54) POLYMERS FOR INCREASING THE SOIL MOBILITY OF LOW-SOLUBILITY INSECTICIDES

(75) Inventors: Michael Ishaque, Mannheim (DE); Marc Rudolf Jung, Worms (DE); Holger Tuerk, Mannheim (DE); Tina Schroeder-Grimonpont, Rheinzabern (DE); Klaus Reinhard, Roemerberg (DE); Gerhard Schnabel, Elsenfeld (DE); Clark D. Klein, Pittsboro, NC (US); Thomas J. Holt, Holly Springs, NC (US); Martin P. Mascianica, Chapel Hill, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/319,467

(22) PCT Filed: May 10, 2010

(86) PCT No.: PCT/EP2010/056348

§ 371 (c)(1),
(2), (4) Date: Nov. 8, 2011

(87) PCT Pub. No.: WO2010/130680

PCT Pub. Date: Nov. 18, 2010

(65) Prior Publication Data

US 2012/0053221 A1 Mar. 1, 2012

Related U.S. Application Data

(60) Provisional application No. 61/177,030, filed on May 11, 2009.

(30) Foreign Application Priority Data

Jun. 24, 2009 (EP) .................................... 09163674

(51) Int. Cl.
*A01N 43/56* (2006.01)
*A01P 7/04* (2006.01)
*A01N 25/30* (2006.01)

(52) U.S. Cl.
CPC .................................. *A01N 25/30* (2013.01)

(58) Field of Classification Search
CPC ........ A01N 25/30; A01N 37/28; A01N 43/36; A01N 43/40; A01N 43/54; A01N 43/56; A01N 43/58; A01N 47/02; A01N 47/34; A01N 47/38; A01N 51/00; A01N 53/00; A01N 57/16
USPC ........................................................ 514/407
See application file for complete search history.

(56) References Cited

U.S. PATENT DOCUMENTS

| | | | | |
|---|---|---|---|---|
| 4,303,642 | A | 12/1981 | Kangas | |
| 6,075,107 | A * | 6/2000 | Kothrade | A61K 47/32 526/258 |
| 2008/0153925 | A1 | 6/2008 | Pierobon et al. | |
| 2009/0041813 | A1 * | 2/2009 | Bouillo et al. | 424/401 |
| 2010/0047203 | A1 | 2/2010 | Dieckmann et al. | |
| 2010/0048655 | A1 | 2/2010 | Koltzenburg et al. | |
| 2010/0179198 | A1 | 7/2010 | Mertoglu et al. | |
| 2010/0204045 | A1 | 8/2010 | Dieckmann et al. | |

FOREIGN PATENT DOCUMENTS

| | | | | |
|---|---|---|---|---|
| EP | 0649649 | | | 4/1995 |
| WO | WO 03/053345 | | | 7/2003 |
| WO | WO 03053345 | A2 | * | 7/2003 |
| WO | WO 2006/018135 | | | 2/2006 |
| WO | WO 2006/087227 | | | 8/2006 |
| WO | WO 2006087227 | A2 | * | 8/2006 |
| WO | WO 2008/040786 | | | 4/2008 |
| WO | WO 2008/058848 | | | 5/2008 |
| WO | WO 2008/064986 | | | 6/2008 |
| WO | WO 2008/064987 | | | 6/2008 |
| WO | WO 2008/064990 | | | 6/2008 |
| WO | WO 2008/065050 | | | 6/2008 |
| WO | WO 2008064986 | A1 | * | 6/2008 |
| WO | WO 2008064990 | A2 | * | 6/2008 |
| WO | WO 2008065050 | A1 | * | 6/2008 |
| WO | WO 2009/007328 | | | 1/2009 |
| WO | WO 2009/021986 | | | 2/2009 |
| WO | WO 2009021986 | A1 | * | 2/2009 |
| WO | WO 2009/040248 | | | 4/2009 |
| WO | WO 2009040248 | A1 | * | 4/2009 |
| WO | WO 2010/130599 | | | 11/2010 |

OTHER PUBLICATIONS

Le Garrec et al.,J Control Release. Sep. 14, 2004;99(1):83-101.*
BASF, Solubility Enhancement with BASF Pharma Polymers-Solubilizer Compendium [online],Oct. 2011 [retrieved on Sep. 26, 2014]. Retrieved from the Internet:< URLhttp://www.pharma-ingredients.basf.com/documents/enp/brochure/en/b_03_110921e_solubility_enhance_compendium.pdf>.*
International Search Report in International Application No. PCT/EP2010/056001, filed May 4, 2010.
English language translation of the International Preliminary Report on Patentability from corresponding International Application No. PCT/EP2010/056001, filed May 4, 2010.
Odian, "Principles of Polymerization," 3rd ed., (1991), pp. 719-720.

* cited by examiner

*Primary Examiner* — Johann R Richter
*Assistant Examiner* — Courtney Brown
(74) *Attorney, Agent, or Firm* — Brinks Gilson & Lione

(57) ABSTRACT

What is described is use of a polymeric solubilizer for increasing the soil mobility of a sparingly soluble insecticide, said polymeric solubilizer having the property that the active insecticidal ingredient in a 1% by weight aqueous solution of the polymeric solubilizer at 25° C. and 1.01325 bar has a solubility at least forty times higher than under the same conditions in pure water, and wherein the active ingredient:solubilizer weight ratio is ≤1.

18 Claims, No Drawings

POLYMERS FOR INCREASING THE SOIL MOBILITY OF LOW-SOLUBILITY INSECTICIDES

This application is a National Stage application of International Application No. PCT/EP2010/056348, filed May 10, 2010 which claims the benefit of U.S. Provisional Application No. 61/177,030 filed May 11, 2009, the entire contents of which are hereby incorporated herein by reference. This application also claims priority under 35 U.S.C. §119 to European Patent Application No. 09163674.6 filed Jun. 24, 2009, the entire contents of which is hereby incorporated herein by reference.

The invention relates to the use of particular polymers for increasing the soil mobility of insecticides with low water solubility, to active insecticidal ingredient compositions with increased soil mobility, and to a method for controlling soil-dwelling pests, especially termites.

Many pesticides comprise active ingredients which have barely any soil mobility or none whatsoever after application. In particular cases, however, increased and controlled soil mobility is advantageous, for example in the control of soil-dwelling pests, especially termites.

When the intention is to transfer active ingredients with low soil mobility into deeper soil layers (in a controlled manner), the options available are almost exclusively mechanical: the digging of trenches and direct treatment of the trench walls, and the spraying of the active ingredient formulation under pressure into deeper soil layers are examples thereof. Such methods require a high degree of labor and/or equipment.

In addition, the use of particular formulation aids is also known, in order to increase the soil mobility of active ingredients. WO 03/053345 describes the use of specific formulation aids (adjuvants), with which the soil mobility of particular active ingredients, especially pyrethroids, is improved by at least 20%. The adjuvants include polymers, such as modified polyethers. U.S. Pat. No. 4,303,642 describes polymer latices for improving the soil mobility of chlorpyrifos and chlorpyrifos-methyl.

Even though good results are already achieved with the systems described, there is a great deal of room for improvement.

It is an object of the invention to provide compounds which improve the soil mobility of sparingly soluble insecticides which have high absorptivity in soil, such that the active ingredient gets into deeper soil layers with reduced labor, if any.

It has been found that the soil mobility of sparingly soluble insecticides can be increased when the active ingredient is used in combination with a polymeric solubilizer.

WO 2008/064990, WO2008/065050, WO 2008/064986, WO 2008/064987, WO 2008/040786, WO 2008/058848 and WO 2006/018135 already disclose that particular polymers increase the water solubility and/or systemic action of fipronil and other insecticides.

Since the soil mobility of an active ingredient, however, depends significantly on the so-called soil absorption coefficient $K_{o/c}$, an increased water solubility does not lead to better soil mobility.

The invention therefore provides for the use of a polymeric solubilizer for increasing the soil mobility of a sparingly soluble insecticide, wherein the polymeric solubilizer has the property that the active insecticidal ingredient in a 1% by weight aqueous solution of the polymeric solubilizer at 25° C. and 1.01325 bar has a solubility at least forty times higher than under the same conditions in pure water, and wherein the weight ratio of active ingredient to solubilizer is ≤1.

The invention further provides a method for improving the soil mobility of sparingly soluble insecticides, wherein the sparingly soluble active insecticidal ingredient and a polymeric solubilizer which has the property that the active insecticidal ingredient in a 1% by weight aqueous solution of the polymeric solubilizer at 25° C. and 1.01325 bar has a solubility at least forty times higher than under the same conditions in pure water, in a weight ratio of ≤1, are applied to the soil to be treated in an aqueous application form.

The invention enables a significant increase in the soil mobility of sparingly soluble active insecticidal ingredients, especially those with a high $K_{o/c}$, value. The inventive combinations of active ingredient and solubilizer, when applied to the soil, additionally exhibit increased biological activity. Moreover, the physical stability of the formulations and of the spray liquors obtained therefrom is improved.

In the context of the invention, the term "insecticide" comprises, unless evident from the context, not only insecticides in the narrower sense, i.e. active ingredients suitable for controlling insects, but also further active ingredients suitable for controlling soil-dwelling invertebrate pests, especially nematicides and acaricides.

A termiticide in the context of the invention is an active insecticidal ingredient suitable for controlling termites.

Unless evident otherwise from the context, the term "sparingly soluble" relates to the solubility in water and means in the context of the invention that the active insecticidal ingredient has a water solubility of less than 1 g/l, preferably less than 0.65 g/l, more preferably less than 0.1 g/l, especially less than 0.01 g/l, at 25° C. and 1013 mbar.

The sparingly soluble termiticides used in accordance with the invention preferably have a soil absorption coefficient $K_{o/c}$ of >250, more preferably >400.

The $K_{o/c}$ describes the distribution of an active ingredient between the organic component of the soil and an aqueous solution. High $K_{o/c}$ values show strong binding of the active ingredients to the organic soil substance; the soil mobility is therefore lower than in the case of those active ingredients with lower $K_{o/c}$ values. The $K_{o/c}$ value is calculated by the formula:

$$K_{o/c}=K_d\times 100/C_{org}[\%]$$

where the $K_d$ value denotes the soil/water partition coefficient for an active ingredient equilibrium and $C_{org}$ the carbon content of the soil in %.

The experimental procedure in $K_{o/c}$ value determinations is described in detail in OECD guideline no. 106. In this procedure, a suspension of soil and 0.01 M $CaCl_2$ solution is prepared. To this suspension is added (preferably radiolabeled) active ingredient in (in the simplest case) one concentration dissolved in a very small amount of organic solvent, and the mixture is shaken gently. When an equilibrium of the concentrations of the active ingredient in the two phases has formed after a few hours, the concentration in the soil and in the $CaCl_2$ solution is determined. The quotient of the concentrations in the soil and in the $CaCl_2$ solution are used to obtain the $K_d$ value, from which the $K_{o/c}$ value for the particular soil results taking account of the organic carbon content of the soil. According to the invention, standard soil is considered to be "LUFA 2.3" soil (sandy loam [according to USDA classification] with a pH of approx. 7 [measured in $CaCl_2$] and an organic carbon content of approx. 1.1%).

Low-mobility active ingredients are considered to be those having a $K_{o/c}$ value of >250.

Preference is give to the use of an insecticide having a water solubility of <1.0 g/l at 25° C. and 1013 mbar and a $K_{o/c}$ value of >250.

Preference is given to use of a sparingly soluble insecticide, especially termiticide, from the group of fipronil, pyrethroide, 4-chloro-2-(2-chloro-2-methylpropyl)-5-[(6-iodo-3-pyridinyl)methoxy]-3(2H)-pyridazinone (CAS-RN: 120955-77-3), chlorantraniliprole, chlorfenapyr, chlorpyrifos, cyantraniliprole, fenoxycarb, flufenoxuron, hydramethylnon, imidacloprid, indoxacarb, metaflumizone, pyriproxifen and tebufenozide.

Preferred termiticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl) methoxy]-3(2H)-pyridazinone (CAS-RN: 120955-77-3), chlorantraniliprole, chlorfenapyr, chlorpyrifos, cyantraniliprole, cyfluthrin, cyhalothrin, cypermethrin, deltamethrin, etofenprox, fenoxycarb, flufenoxuron, hydramethylnon, imidacloprid, indoxacarb, metaflumizone, permethrin, pyriproxifen, tebufenozide and tralomethrin.

Particular preference is given to fipronil, alpha-cypermethrin, bifenthrin, chlorantraniliprole, chlorfenapyr, cyfluthrin, cypermethrin, cyantraniliprole, deltamethrin, etofenprox, hydramethylnon, indoxacarb, metaflumizone and permethrin.

Very particular preference is given to fipronil, alpha-cypermethrin, chlorantraniliprole, chlorfenapyr, cyantraniliprole, deltamethrin, hydramethylnon, indoxacarb and metaflumizone.

Fipronil is especially preferred.

Preference is given to the use of one (1) sparingly soluble active insecticidal ingredient.

Additionally preferred is the use of two or more, more preferably two or three, sparingly soluble active insecticidal ingredients, especially of mixtures of the insecticides mentioned.

Preference is given to the use of fipronil in a mixture with one or more pyrethroids, especially alpha-cypermethrin and/or deltamethrin, or metaflumizone or borates.

If appropriate, the sparingly soluble active insecticidal ingredient used in accordance with the invention can also be used in a mixture with further active pesticidal ingredients, especially further active insecticidal or fungicidal ingredients. Preference is given, for example, to a mixture of fipronil and metaflumizone.

The active pesticidal, especially insecticidal, ingredients mentioned are commercially available and are described, for example, in C.D.S. Tomlin (ed.), The Pesticide Manual, 14th edition, British Crop Production Council, Alton 2006. Cyantraniliprole is 3-bromo-N-[4-cyano-2-methyl-6-(methylcarbamoyl)phenyl]-1-(3-chloropyridin-2-yl)-1H-pyrazole-5-carboxamide (DPX-HGW86, Cyazypyr®).

To increase the soil mobility of the sparingly soluble insecticide, one or more polymeric solubilizers are used in accordance with the invention.

According to the invention, "polymeric solubilizer" means a polymer, preferably having a molar mass $M_n$, of >1000 g/mol, which has the property that the active insecticidal ingredient in a 1% by weight aqueous solution of the polymeric solubilizer at 25° C. and 1013 mbar has a solubility at least forty times, preferably fifty times, higher than under the same conditions in pure water.

For a particular polymer, qualification as a polymer solubilizer for use in accordance with the invention is thus related to a particular inventive insecticide.

Preferred polymeric solubilizers are polymers in whose 1% by weight aqueous solutions the insecticide fipronil has a solubility of at least 100 mg/l at 25° C. and 1013 mbar.

The solubility can be determined by known methods; according to the invention, a UV spectroscopy measurement is preferred. First, a calibration with the active ingredient to be determined is performed at a suitable wavelength in different concentrations. To study the solubilization with a polymeric solubilizer, a 1% by weight polymer solution is prepared and the UV absorption is measured at said wavelength. The polymer solution is saturated with the active ingredient to be analyzed and equilibrated for 24 h. After centrifugation of the solution and UV analysis of the supernatant at said wavelength, after subtracting the polymer absorption over the calibration curve, the dissolved active ingredient concentration can be concluded.

Solubilization is understood to mean solubilization of substances which are sparingly soluble or insoluble in a particular solvent, especially water, by interface-active compounds, the solubilizers. Solubilizers are capable of converting sparingly water-soluble or water-insoluble active ingredients to clear, at worst opalescent aqueous solutions, without the chemical structure of these substances undergoing any change in the process (cf. Römpp Chemie Lexikon, 9th edition, vol. 5, p. 4203, Thieme Verlag, Stuttgart, 1992).

In the solubilizates produced, the sparingly water-soluble or water-insoluble substance is present in colloidally dissolved form in the molecular associates of the surface-active compounds which form in aqueous solution, for example hydrophobic domains or micelles. The resulting solutions are stabile or metastable monophasic systems which have a visually clear to opalescent appearance.

The solubilizers used in accordance with the invention preferably bring about an improvement in the vertical and/or horizontal soil mobility of the active ingredient by 20%, more preferably 50%, especially 100%, compared to an identical application without polymeric solubilizer.

Preferred polymeric solubilizers are those of groups A to H:

A. hyperbranched polymers from the group of the polycarbonates, polyureas, polyamides, polythioureas, polyurethanes, polyesters, polyethers, polyestercarbonates, polyethercarbonates, polyetheresters, polyesteramides, polyesteramines, polyetherestercarbonates and polyetherurethanecarbonates, said polymers having a weight-average molecular weight ($M_W$) of at least 500 g/mol, the main chain thereof being branched and said polymers having a degree of branching (DB) of at least 0.05;

B. vinyllactam copolymers from the group of

B1. vinyllactam copolymers obtainable from

B1-1. 60-99% by weight (based on the overall copolymer) of 5-7-membered 1-vinyl-2-lactam and B1-2. 1 to 40% by weight of at least one monomer selected from the group of the B1-21 $C_8$-$C_{30}$-alkyl esters of monoethylenically unsaturated $C_3$-$C_8$-carboxylic acids, B1-22 N-alkyl- or N,N-dialkyl-substituted amides of acrylic acid or of methacrylic acid having $C_8$ to $C_{30}$-alkyl radicals, B1-23 vinyl esters of aliphatic unbranched $C_8$-$C_{30}$-carboxylic acids, B1-24 the $C_8$-$C_{30}$-alkyl vinyl ethers, where the percentages by weight of the individual components add up to 100% by weight;

B2. polyvinyl lactam-polyvinyl acetate block copolymers;

B3. vinyllactam copolymers comprising polyalkylene oxide (monoalkyl ether)-modified side chains;

B4. vinyllactam copolymers obtainable from

B4-1. N-vinyllactam monomers of the formula (I)

(I)

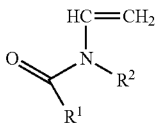

where the symbols are each defined as follows $R^1$ and $R^2$ together form a $—(CH_2)_x$ group which, together with the nitrogen and the carboxyl group, forms a 5-8-membered ring, and B4-2. at least one monomer from the group of vinylpyridine, vinylpyridine derivatives and N-vinylimidazole;

B5. copolymers obtainable by polymerizing

B5-1. at least one compound of the formula (II) (monomer A)

(II)

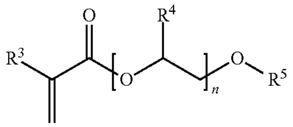

where $R^3$ and $R^4$ are each independently H or $CH_3$, $R^5$ is $C_6$-$C_{10}$-aryl or $C_7$-$C_{12}$-aralkyl, each of which may bear one or more identical or different $C_1$-$C_9$-alkyl and/or $C_1$-$C_5$-alkoxy substituents, and n is 0 to 100, preferably 1 or 2, B5-2. at least one compound selected from the group of the N-vinyllactams (monomer B), B5-3. if appropriate one or more different difunctional crosslinker components and B5-4. if appropriate one or more different regulators and B5-5. if appropriate one or more further copolymerizable components (monomer C);

C. copolymers based on diisocyanates of the formula (III)

(III)

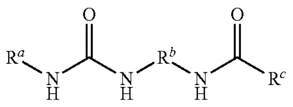

wherein the symbols are each defined as follows:

$R^a$ is unbranched or branched $C_4$-$C_{24}$-alkyl, $C_3$-$C_8$-cycloalkyl, $C_3$-$C_8$-cycloalkyl substituted by $C_1$-$C_6$-alkyl, phenyl, phenyl substituted by $C_1$-$C_6$-alkyl, benzyl, benzyl substituted by $C_1$-$C_6$-alkyl, $C_4$-$C_6$-alkyl substituted by $C_4$-$C_{12}$-alkoxy, or $C_1$-$C_4$-alkyl substituted by di($C_1$-$C_4$-alkyl)amino;

$R^b$ is derived from a diisocyanate;

$R^c$ is a group of the formula (IV), $$(R^6)_n—X—(CHR^7CH_2O)_w—(CHR^8CH_2O)_x—(CHR^9(CH_2)_yO)_z— \quad (IV)$$

$R^6$ is $H_x$ or unbranched or branched, saturated or unsaturated $C_1$-$C_{40}$-alkyl;

$R^7$, $R^8$, $R^9$ are each independently H or $C_1$-$C_4$-alkyl;

w, x, z are each independently integers from 0 to 300;

y is an integer from 1 to 20;

X is N or O;

D. copolymers based on ethylenically unsaturated dicarboxylic mono- and diesters, obtainable from D1 at least one monomer from the group of the olefins, vinyl ethers and styrene and D2 at least one monomer from the group of the mono- and diesters of ethylenically unsaturated dicarboxylic acids, where the alcohol group of the ester has a structure of the formula (V)

$$—(R^{10}—O)_n—(R^{11}—O)_p—R^{12} \quad (V)$$

where the symbols and indices are each defined as follows:

$R^{10}$ is 1,2-propylene or 2,3-propylene;

$R^{11}$ is ethylene;

$R^{12}$ is H, unbranched or branched $C_1$-$C_{40}$-alkyl, preferably $C_1$-$C_{24}$-alkyl, phenyl, phenyl substituted by $C_1$-$C_{20}$-alkyl, benzyl, benzyl substituted by $C_1$-$C_{20}$-alkyl;

n is an integer from 0 to 140, preferably 0 to 50, more preferably 0 to 20, and p is an integer from 0 to 100, where the sum of n and p is at least 1, preferably 1 to 60 and more preferably 5 to 40;

E. vinylamide copolymers obtainable from

E1. N-vinylamide monomers of the formula (VI)

(VI)

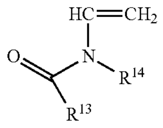

wherein the symbols are each defined as follows $R^{13}$, $R^{14}$ are each independently H or $C_1$-$C_4$-alkyl, preferably H, and E2. at least one monomer from the group of vinylpyridine, vinylpyridine derivatives and N-vinylimidazole;

F. comb polymers obtainable by copolymerizing monoethylenically unsaturated monomers M, comprising:

F1. at least one monoethylenically unsaturated monomer Ma, selected from esters of monoethylenically unsaturated $C_3$-$C_8$-monocarboxylic acids with $C_1$-$C_{20}$-alkanols, $C_5$-$C_{10}$-cycloalkanols, phenyl-$C_1$-$C_4$-alkanols or phenoxy-$C_1$-$C_4$-alkanols, and the diesters of monoethylenically unsaturated $C_4$-$C_8$-dicarboxylic acids with $C_1$-$C_{20}$-alkanols, $C_5$-$C_{10}$-cycloalkanols, phenyl-$C_1$-$C_4$-alkanols or phenoxy-$C_1$-$C_4$-alkanols;

F2. at least one monoethylenically unsaturated monomer Mb selected from the esters of monoethylenically unsaturated $C_3$-$C_8$-monocarboxylic acids and the mono- and diesters of monoethylenically unsaturated $C_4$-$C_8$-dicarboxylic acids with poly-($C_2$-$C_4$-alkylene ether)ols;

where the total amount of monomers Ma and Mb makes up at least 60% by weight of the monomers M which constitute the comb polymers;

G. copolymers obtainable from

G1. 5 to 99% by weight of at least one N-vinylcarboxamide of the formula (VII)

(VII)

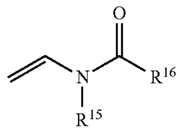

in which $R^{15}$ and $R^{16}$ are each independently hydrogen or $C_1$-$C_6$-alkyl;

G2. 1 to 95% by weight of at least one monomer which has a hydrophobic radical, is copolymerizable with vinylcarboxamides of the formula (V) and is selected from G21. esters of monoethylenically unsaturated $C_3$-$C_8$-carboxylic acids with aliphatic or cycloaliphatic $C_8$-$C_{30}$-alcohols;

G22. amides of monoethylenically unsaturated $C_3$-$C_8$-carboxylic acids with primary or secondary amines having at least one aliphatic or cycloaliphatic $C_8$-$C_{30}$ radical;

G23. vinyl esters of aliphatic or cycloaliphatic $C_8$-$C_{30}$-carboxylic acids; or G24. vinyl ethers of aliphatic or cycloaliphatic $C_8$-$C_{30}$-alcohols; and if appropriate G3. 0 to 94% by weight of at least one further copolymerizable monomer;

H. copolymers obtainable by free-radical copolymerization of

H1. acrylamidopropylmethylenesulfonic acid (AMPS) and/or salts thereof;

H2. one or more macromonomers comprising i) an end group which is capable of polymerization and is at least partially soluble in the reaction medium, ii) a hydrophobic moiety which is hydrogen or a saturated or unsaturated, linear or branched, aliphatic, cycloaliphatic or aromatic ($C_1$-$C_{100}$) hydrocarbon radical, and iii) a hydrophilic moiety based on polyalkylene oxides; and H3. optionally one or more further, at least mono- or polyolefinically unsaturated oxygen-, nitrogen-, sulfur-, phosphorus-, chlorine- and/or fluorine-containing comonomers.

Group A

Hyperbranched polycarbonates, polyureas, polyamides, polythioureas, polyurethanes, polyesters, polyethers, polyestercarbonates, polyethercarbonates, polyetheresters, polyesteramides, polyesteramines, polyetherestercarbonates and polyetherurethanecarbonates, and the preparation thereof, are described, for example, in WO 2009/021986.

Preference is given to hyperbranched polycarbonates (A1) which are described with their preparation in European patent application EP 09159881.3, filed on the same date, with the title "Hyperbranched polycarbonates for solubilizing sparingly soluble active ingredients", and in which the hyperbranched polycarbonate is joined to at least one linear or comb-type polymer and/or at least one functional $C_1$-$C_{24}$ unit comprising an acid group, an amino group or at least two hydroxyl groups.

Preference is given to hyperbranched polycarbonates A1 in which the polycarbonate comprises an alcohol A which is a trifunctional or higher-functionality polyetherol based on alcohols which have at least three OH groups, and $C_3$-$C_{24}$ alkylene oxide.

Preference is given especially to hyperbranched polycarbonates A1 in which the linear polymer is a) a homopolymer or random copolymer comprising a polar ethylenically unsaturated monomer, b) a block polymer comprising a block of polyethylene glycol or based on a polar ethylenically unsaturated monomer, or c) a polycondensate comprising polyethylene glycol, or d) a polyethylene glycol, the polyethylene glycol d) being jointed to the polycarbonate via a linker, preferably a carbonate, urea or urethane group, more preferably a urethane group.

Preference is also given to hyperbranched polycarbonates A1 in which the polar ethylenically unsaturated monomer is vinylpyrrolidone, (meth)acrylic acid, a sulfonic acid-containing monomer, an amino-functional monomer or a (meth)acrylic ester of a polyethylene glycol derivative.

Preference is also given to hyperbranched polycarbonates A1 in which the comb-type polymer comprises polyethylene glycol mono(meth)acrylate or allyl alcohol alkoxylate in polymerized form.

Preference is also given to hyperbranched polycarbonates A1 in which the functional $C_1$-$C_{24}$ unit comprises a carboxylic acid group, a sulfonic acid group, a sulfenic acid group, a sulfinic acid group, a sulfuric ester group (i.e. an organic sulfate), an amino group or at least two hydroxy-$C_2$-$C_{10}$-alkyl groups.

Preference is also given to hyperbranched polycarbonates A1 in which the amphiphile comprises a hyperbranched polycarbonate which is joined to at least one linear or comb-type polymer.

Preference is also given to hyperbranched polycarbonates A1 in which the polycarbonate is joined to at least one linear or comb-type polymer, wherein the linear polymer is a) a homopolymer or random copolymer comprising a polar ethylenically unsaturated monomer, b) a block polymer comprising a block of polyethylene glycol or based on a polar ethylenically unsaturated monomer, or c) a polycondensate comprising polyethylene glycol, or d) a polyethylene glycol, the polyethylene glycol d) being joined to the polycarbonate via a linker, preferably a carbonate, urea or urethane group, more preferably a urethane group.

Preference is also given to hyperbranched polycarbonates A1 in which the polycarbonate is obtainable by a) preparing a condensation product (K) by reacting an organic carbonate (A) or a phosgene derivative with an alcohol (B1) which has at least three hydroxyl groups, and b) intermolecularly converting K to the hyperbranched polycarbonate, the quantitative ratio of the OH groups to the carbonate or phosgene groups being selected such that K has an average of either i) one carbonate or carbamoyl chloride group and more than one OH group, or ii) one OH group and more than one carbonate or carbamoyl group.

Preference is also given to hyperbranched polycarbonates A1 in which the comb-type polymer comprises polyethylene glycol mono(meth)acrylate in polymerized form.

The hyperbranched polycarbonate A1 is typically obtainable by a) preparing a condensation product (K) by reacting an organic carbonate (A) or a phosgene derivative with an alcohol (B1) which has at least three hydroxyl groups, and b) intermolecularly converting K to the hyperbranched polycarbonate, the quantitative ratio of the OH groups to the carbonate or phosgene groups being selected such that K has an average of either i) one carbonate or carbamoyl chloride group and more than one OH group, or ii) one OH group and more than one carbonate or carbamoyl group. The polycarbonate is preferably obtained in this way.

To prepare the condensation product (K), an organic carbonate (A) or a phosgene derivative can be used. Suitable phosgene derivatives are, for example, phosgene, diphosgene or triphosgene, preferably phosgene. Preference is given to using an organic carbonate.

The R radicals of the organic carbonates (A) of the general formula $RO[(CO)O]_nR$ used as starting material are each independently a straight-chain or branched aliphatic, aromatic/aliphatic (araliphatic) or aromatic hydrocarbon radical having 1 to 20 carbon atoms. The two R radicals may also be joined to one another to form a ring. The two R radicals may be the same or different; they are preferably the same. The carbonates may preferably be simple carbonates of the general formula RO(CO)OR, i.e. n in this case is 1.

Examples of suitable carbonates comprise aliphatic, aromatic/aliphatic or aromatic carbonates. Preference is given to using aliphatic carbonates, especially those in which the radicals comprise 1 to 5 carbon atoms, for example dimethyl carbonate, diethyl carbonate, di-n-propyl carbonate, di-n-butyl carbonate or diisobutyl carbonate. Diethyl carbonate is especially preferred.

The alcohol (B1) which has at least three hydroxyl groups is usually an aliphatic or aromatic alcohol, or a mixture or two or more different alcohols of this kind. The alcohol (B1) may be branched or unbranched, substituted or unsubstituted, and have 3 to 26 carbon atoms. It is preferably an aliphatic alcohol. Examples of compounds having at least three OH groups comprise glycerol, trimethylolmethane, trimethylolethane, trimethylolpropane, trimethylolbutane, 1,2,4-butanetriol, 1,2,3-hexanetriol, 1,2,4-hexanetriol, tris(hydroxymethyl)amine, tris(hydroxyethyl)amine, tris(hydroxypropyl)amine, pentaerythritol, diglycerol, triglycerol, polyglycerols, bis(trimethylolpropane), tris(hydroxymethyl) isocyanurate, tris(hydroxyethyl) isocyanurate, phloroglucinol, trihydroxytoluene, trihydroxydimethylbenzene, phloroglucides, hexahydroxybenzene, 1,3,5-benzenetrimethanol, 1,1,1-tris(4'-hydroxyphenyl)methane, 1,1,1-tris(4'-hydroxyphenyl)ethane, sugars, for example glucose, sugar derivatives, for example sorbitol, mannitol, diglycerol, threitol, erythritol, adonitol (ribitol), arabitol (lyxitol), xylitol, dulcitol (galactitol), maltitol, isomaltitol, or polyesterol. In addition, B1 may be a trifunctional or higher-functionality polyetherol based on alcohols which have at least three OH groups, and $C_2$-$C_{24}$ alkylene oxide. The polyetherol especially comprises usually an average of one to 30, preferably one to 20, more preferably one to 10 and most preferably one to eight molecules of ethylene oxide and/or propylene oxide and/or isobutylene oxide per hydroxyl group.

The hyperbranched polycarbonate preferably comprises an alcohol (B1) which is a trifunctional or higher-functionality polyetherol based on alcohols which have at least three OH groups, and $C_3$-$C_{24}$ alkylene oxide. Suitable alcohols, at least three OH groups, are as described above, preferably glycerol, trimethylolethane, trimethylolpropane, 1,2,4-butanetriol, 1,2,3-hexanetriol, 1,2,4-hexanetriol, pentaerythritol, more preferably glycerol and trimethylolpropane. Preferred $C_3$-$C_{24}$ alkylene oxides include propylene oxide, butylene oxide, pentylene oxide and mixtures thereof, more preferably propylene oxide. The trifunctional or higher-functionality polyetherols usually comprise one to 30, preferably two to 30, more preferably three to 20 $C_3$-$C_{24}$ alkylene oxide molecules in polymerized form. A particularly preferred alcohol (B1) is a trifunctional polyetherol based on glycerol, trimethylolethane, trimethylolpropane, 1,2,4-butanetriol and/or pentaerythritol, and propylene oxide, where the polyetherol comprises at least three, preferably three to 30, more preferably three to 20, molecules of propylene oxide in polymerized form.

In addition to the alcohol (B1), the polycarbonate A1 may have a difunctional alcohol (B2) as a forming component, with the proviso that the mean OH functionality of all alcohols B used together is greater than 2. The alcohols (B1) and (B2) are referred to here together as (B). Suitable difunctional alcohols B2 include diethylene glycol, triethylene glycol, 1,2- and 1,3-propanediol, dipropylene glycol, tripropylene glycol, neopentyl glycol, 1,2-, 1,3- and 1,4-butanediol, 1,2-, 1,3- and 1,5-pentanediol, 1,6-hexanediol, 1,2-, 1,3- or 1,4-cyclohexanediol, 1,1-, 1,2-, 1,3- or 1,4-cyclohexanedimethanol, bis(4-hydroxycyclohexyl)methane, difunctional polyetherpolyols based on ethylene oxide, propylene oxide, butylene oxide or mixtures thereof, polytetrahydrofuran having a molar mass of 162 to 2000, polycaprolactone or polyesterols based on diols and dicarboxylic acids. Preferred difunctional alcohols (B2) are difunctional polyetherpolyols based on ethylene oxide, propylene oxide, butylene oxide or mixtures thereof, and polyesterols based on diols and dicarboxylic acids.

The diols serve for fine adjustment of the properties of the polycarbonate A1. If difunctional alcohols are used, the ratio of difunctional alcohols (B2) to the at least trifunctional alcohols (B1) is fixed by the person skilled in the art according to the desired properties of the polycarbonate. In general, the amount of the alcohol(s) (B2) is 0 to 50 mol % based on the total amount of all alcohols (B1) and (B2) together. The amount is preferably 0 to 35 mol %, more preferably 0 to 25 mol % and most preferably 0 to 10 mol %.

The reaction of phosgene, diphosgene or triphosgene with the alcohol or alcohol mixture is generally effected with elimination of hydrogen chloride; the reaction of the carbonates with the alcohol or alcohol mixture to give the inventive high-functionality highly branched polycarbonate is effected with elimination of the monofunctional alcohol or phenol from the carbonate molecule.

After this reaction, i.e. without any further modification, the hyperbranched polycarbonate has high-functionality termination with hydroxyl groups and with carbonate groups or carbamoyl chloride groups. A high-functionality polycarbonate is understood to mean a product which, as well as the carbonate groups which form the polymer skeleton, additionally has, in terminal or lateral position, at least three, preferably at least four and more preferably at least six functional groups. The functional groups are carbonate groups or carbamoyl chloride groups and/or OH groups. There is in principle no upper limit in the number of terminal or lateral functional groups, but products with a very high number of functional groups may have undesired properties, for example high viscosity and poor solubility. The high-functionality polycarbonates of the invention usually have not more than 500 terminal or lateral functional groups, preferably not more than 100 terminal or lateral functional groups.

In the preparation of the high-functionality polycarbonates, it is necessary to adjust the ratio of the compounds comprising OH groups to phosgene or carbonate (A) such that the resulting simplest condensation product (known hereinafter as condensation product (K)) comprises an average of either i) one carbonate or carbamoyl chloride group and more than one OH group or ii) one OH group and more than one carbonate or carbamoyl chloride group, preferably an average of either i) one carbonate or carbamoyl chloride group and at least two OH groups or ii) one OH group and at least two carbonate or carbamoyl chloride groups.

It may additionally be advisable, for fine adjustment of the properties of the polycarbonate, to use at least one difunctional carbonyl-reactive compound (A1). This is understood to mean those compounds which have two carbonate and/or carboxyl groups. Carboxyl groups may be carboxylic acids, carbonyl chlorides, carboxylic anhydrides or carboxylic esters, preferably carboxylic anhydrides or carboxylic esters and more preferably carboxylic esters. If such difunctional compounds (A1) are used, the ratio of (A1) to the carbonates or phosgenes (A) is fixed by the person skilled in the art according to the desired properties of the polycarbonate. In general, the amount of the divalent compound(s) (A1) is 0 to 40 mol % based on the total amount of all carbonates/phosgenes (A) and compounds (A1) together. Examples of compounds (A1) are dicarbonates or dicarbamoyl chlorides of diols. Further compounds (A1) are dicarboxylic acids and/or esters of dicarboxylic acids.

The simplest structure of the condensation product (K), shown by the example of the reaction of a carbonate (A) with a di- or polyalcohol (B) gives rise to the arrangement $XY_m$ or $Y_mX$, where X is a carbonate or carbamoyl group, Y is a hydroxyl group and m is generally an integer greater than 1 to 6, preferably greater than 1 to 4, more preferably greater than 1 to 3. The reactive group, which results in this case as a single group, is generally known hereinafter as "focal group".

It is also possible to use a plurality of condensation products (K) for the synthesis. In this case, it is possible either to use a plurality of alcohols or a plurality of carbonates.

In addition, the selection of the ratio of the alcohols used and of the carbonates or of the phosgenes allows mixtures of different condensation products of different structure to be obtained.

Typical reaction conditions of the reaction of (A) with (B) to give the condensation product (K) are detailed hereinafter:

The stoichiometry of components (A) and (B) is generally selected such that the resulting condensation product (K) has either one carbonate or carbamoyl chloride group and more than one OH group, or one OH group and more than one carbonate or carbamoyl chloride group. This is achieved in the first case by a stoichiometry of 1 mol of carbonate groups:>2 mol of OH groups, for example a stoichiometry of 1:2.1 to 8, preferably 1:2.2 to 6, more preferably 1:2.5 to 4 and most preferably 1:2.8 to 3.5. In the second case, this is achieved by a stoichiometry of more than 1 mol of carbonate groups:<1 mol of OH groups, for example a stoichiometry of 1:0.1 to 0.48, preferably 1:0.15 to 0.45, more preferably 1:0.25 to 0.4 and most preferably 1:0.28 to 0.35.

The temperature should be sufficient for the reaction of the alcohol with the carbonyl component in question. In general, for the reaction with a phosgene, a temperature of −20° C. to 120° C., preferably 0 to 100 and more preferably 20 to 80° C. is sufficient. In the case of use of a carbonate, the temperature should be 60 to 280° C., preferably 80 to 250° C., more preferably 100 to 250 and most preferably 120 to 250° C.

The preparation is usually effected within a pressure range from 0.1 mbar to 20 bar, preferably at 1 mbar to 5 bar, in reactors or reactor cascades, which are operated in batchwise, semicontinuous or continuous mode.

Useful solvents include aromatic and/or (cyclo)aliphatic hydrocarbons and mixtures thereof, halogenated hydrocarbons, ketones, esters and ethers, preferably butyl acetate, dimethylformamide, dimethylacetamide, dimethyl sulfoxide, methoxypropyl acetate, isobutyl methyl ketone, 2-butanone, aromatic hydrocarbons (such as Solvesso® brands), cyclohexane, chlorobenzene and xylene. A preferred embodiment is to perform the reaction without solvent.

The sequence of addition of the individual component usually plays a minor role. In general, it is advisable to initially charge the excess component of the two reactants and to add the deficiency component. Alternatively, it is likewise possible to mix the two components with one another before the start of the reaction and then to heat this mixture to the required reaction temperature.

According to the invention, the simple condensation products (K) preferably immediately react further intermolecularly to form high-functionality polycondensation products, known hereinafter as polycondensation products (P). The conversion to the condensation product (K) and to the polycondensation product (P) is effected typically at a temperature of 0 to 300° C., preferably 0 to 250° C., more preferably at 60 to 250° C. and most preferably at 80 to 250° C., in bulk or in solution. It is generally possible to use all solvents which are inert toward the particular reactants. Preference is given to using organic solvents, for example those mentioned above and more preferably decane, dodecane, cyclohexane, benzene, toluene, chlorobenzene, xylene, dimethylformamide, dimethylacetamide, dimethyl sulfoxide or solvent naphtha. In a preferred embodiment, the condensation reaction is performed in substance. The monofunctional alcohol or the phenol ROH released in the reaction can be removed from the reaction equilibrium to accelerate the reaction, for example by distillation, if appropriate under reduced pressure.

The removal of the alcohol or phenol can also be supported by passing through a gas stream which is essentially inert under the reaction conditions (stripping), for example nitrogen, steam, carbon dioxide, or else an oxygenus gas, for example air or lean air. If removal by distillation is intended, it is regularly advisable to use those carbonates which, in the reaction, release alcohols or phenols ROH with a boiling point of less than 140° C. at the existing pressure. Alternatively, the alcohols released can be removed by azeotropic distillation by means of entraining agents (e.g. toluene, xylene, chlorobenzene, cyclohexane) or by applying a vacuum, and the formation of the polycondensate can thus be promoted.

To accelerate the reaction, it is also possible to add catalysts or catalyst mixtures. Suitable catalysts are compounds which catalyze esterification or transesterification reactions, for example alkali metal hydroxides, alkali metal carbonates, alkali metal hydrogencarbonates, preferably of sodium, potassium or cesium, tertiary amines, guanidines, ammonium compounds, phosphonium compounds, organoaluminum, -tin, -zinc, -titanium, -zirconium or -bismuth compounds, and additionally so-called double metal cyanide (DMC) catalysts, as described, for example, in DE 10138216 or in DE 10147712. Preference is given to using potassium hydroxide, potassium carbonate, potassium hydrogencarbonate, diazabicyclooctane (DABCO), diazabicyclononene (DBN), diazabicycloundecene (DBU), imidazoles such as imidazole, 1-methylimidazole or 1,2-dimethylimidazole, titanium tetrabutoxide, titanium tetraisopropoxide, dibutyltin oxide, dibutyltin dilaurate, tin dioctoate, zirconium acetylacetonate or mixtures thereof. The catalyst is added generally in an amount of 50 to 10 000 and preferably of 100 to 5000 ppm by weight based on the amount of the alcohol or alcohol mixture used. If appropriate, it may be necessary to predissolve the catalyst in small amounts of a suitable solvent.

In addition, it is also possible to control the intermolecular polycondensation reaction either through addition of the suitable catalyst or through selection of a suitable temperature. Furthermore, the mean molecular weight of the polymer (P) can be adjusted via the composition of the starting components and via the residence time.

The condensation products (K) or the polycondensation products (P) which have been prepared at elevated temperature are stable at room temperature, without exhibiting cloudiness, precipitation and/or a viscosity rise, typically over a prolonged period, for example over at least 6 weeks. Owing to the properties of the condensation products (K), it is possible that the condensation reaction can result in polycondensation products (P) with different structures, which have branches but no crosslinks. In addition, the polycondensation products (P) ideally have either a carbonate or carbamoyl chloride group as the focal group and more than two OH groups or else one OH group as the focal group and more than two carbonate or carbamoyl chloride groups. The number of reactive groups arises from the properties of the condensation products (K) used and the degree of polycondensation.

For termination of the intermolecular polycondensation reaction, there are various possibilities. For example, the temperature can be lowered to a range in which the reaction stops and the product (K) or the polycondensation product (P) is storage-stable. This is the case generally below 60° C., preferably below 50° C., more preferably below 40° C. and most preferably at room temperature. In addition, the catalyst can be deactivated, in the case of basic catalysts for example by addition of an acidic component, for example of a Lewis acid or of an organic or inorganic protic acid. Moreover, it is possible to stop the reaction by diluting with a precooled solvent. This is preferred especially when the viscosity of the reaction mixture has to be adjusted by adding solvent.

In a further embodiment, as soon as a polycondensation product (P) with the desired degree of polycondensation is present owing to the intermolecular reaction of the condensation product (K), a product with groups reactive toward the focal group of (P) can be added to the product (P) to terminate the reaction. For instance, in the case of a carbonate group or carbamoyl group as a focal group, it is possible to add, for example, a mono-, di- or polyamine. In the case of a hydroxyl group as the focal group, for example, a mono-, di- or polyisocyanate, a compound comprising epoxide groups or an acid derivative reactive with OH groups can be added to the product (P).

The aforementioned adjustment of the reaction conditions and if appropriate the selection of the suitable solvent allows the inventive products to be processed further without further purification after the preparation. If required, the reaction mixture can be subjected to a decolorization, for example by treatment with activated carbon or metal oxides. If appropriate, the reaction mixture can also be filtered to remove any precipitates present. In a further preferred embodiment, the product is stripped, i.e. freed of low molecular weight volatile compounds. To this end, on attainment of the desired degree of conversion, the catalyst can optionally be deactivated and the low molecular weight volatile constituents, for example monoalcohols, phenols, carbonates, hydrogen chloride or volatile oligomeric or cyclic compounds, can be removed by distillation, if appropriate with introduction of a gas, preferably nitrogen, carbon dioxide or air, if appropriate under reduced pressure.

The hyperbranched polycarbonates obtainable as described above generally have a glass transition temperature of less than 50° C., preferably less than 30 and more preferably less than 10° C. The OH number is usually 30 mg KOH/g or more, preferably between 50 and 250 mg/g. The weight-average molar mass $M_w$ is usually between 1000 and 150 000, preferably from 1500 to 100 000 g/mol, the number-average molar mass $M_n$ between 500 and 50 000, preferably between 1000 and 40 000 g/mol. The hyperbranched polycarbonate is usually not soluble or dispersible in water, i.e. it is not possible to prepare a clear (i.e. without particles perceptible to the naked eye) aqueous solution or dispersion.

Preference is given to a hyperbranched polycarbonate A1 which is joined to at least one linear or comb-type polymer. The molar ratio of hyperbranched polycarbonate to the sum of linear or comb-type polymer and of functional $C_1$-$C_{24}$ unit is usually in the range from 1:1 to 1:100, preferably 1:1 to 1:50, more preferably 1:1 to 1:25. It is usually joined by means of a linker.

The linear polymer is preferably a) a homopolymer or random copolymer comprising a polar ethylenically unsaturated monomer, b) a block polymer comprising a block of polyethylene glycol or based on at least one polar ethylenically unsaturated monomer, or c) a polycondensate comprising polyethylene glycol, or d) a polyethylene glycol, the polyethylene glycol d) being joined to the polycarbonate via a linker. The linear polymer is more preferably one of the aforementioned polymers a), b) or c). In a further particularly preferred embodiment, the linear polymer is one of the aforementioned polymers a), c) or d). The linear polymer is especially preferably one of the aforementioned polymers a) or c), especially a).

In one embodiment, the linear polymer may be a homopolymer or random copolymer comprising a polar ethylenically unsaturated monomer. The number-average molar mass Mn is usually less than 100 000 g/mol, preferably less than 50 000 g/mol, more preferably less than 20 000 g/mol and most preferably less than 10 000 g/mol, and can be determined by means of GPC and a suitable standard. Mn is typically more than 200 g/mol, preferably more than 500 g/mol.

Suitable polar ethylenically unsaturated monomers are monomers which bear charge or bear ionizable groups and comprise a polymerizable ethylenically unsaturated bond. Examples of charge-bearing or ionizable groups are carboxylic acid, sulfonic acid, polyethylene glycol, alcohol, nitrile, amide, amine, dialkylamine. Examples of polar ethylenically unsaturated monomers are vinylpyrrolidone, (meth)acrylic acid, a sulfo-containing (meth)acrylate (such as 2-acrylamido-2-methylpropanesulfonic acid), an amino-functional (meth)acrylate (such as dimethylaminoethyl (meth)acrylate), (meth)acrylic esters of a polyethylene glycol derivative (such as polyethylene glycol monomethyl ether (meth)acrylate), itaconic acid, maleic anhydride, $C_1$-$C_{20}$-alkyl (meth)acrylates substituted by OH groups (such as hydroxyethyl(meth)acrylate, hydroxybutyl(meth) acrylate), (meth)acrylonitrile, (meth)acrylamide, N-methylol (meth)acrylamide. Preferred polar ethylenically unsaturated monomers are vinylpyrrolidone, (meth)acrylic acid, polyethylene glycol monomethyl ether (meth)acrylate, polyethylene glycol (meth)acrylate. The expression "(meth) acrylic" means "acrylic" or "methacrylic".

Examples of linear homopolymers comprising a polar ethylenically unsaturated monomer are homopolymers of the aforementioned polar ethylenically unsaturated monomers, preferably of vinylpyrrolidone, (meth)acrylic acid, polyethylene glycol monomethyl ether (meth)acrylate, polyethylene glycol (meth)acrylate.

Examples of random copolymers comprising a polar ethylenically unsaturated monomer are copolymers of the aforementioned polar ethylenically unsaturated monomers, preferably of vinylpyrrolidone, (meth)acrylic acid, polyethylene glycol monomethyl ether (meth)acrylate, polyethylene glycol (meth)acrylate. As further monomers, the random copolymer may comprise: esters of acrylic acid with $C_1$-$C_{10}$-alkanols such as ethyl acrylate, n-butyl acrylate, isobutyl acrylate, tert-butyl acrylate, n-hexyl acrylate, 2-ethylhexyl acrylate and 3-propylheptyl acrylate, the esters of methacrylic acid with $C_1$-$C_{10}$-alkanols such as methyl methacrylate, ethyl methacrylate, n-butyl methacrylate, isobutyl methacrylate, tert-butyl methacrylate and n-hexyl methacrylate, N—($C_2$-$C_{10}$-alkyl)amides of acrylic acid and of methacrylic acid, and the N—($C_1$-$C_2$-alkyl)-N—($C_2$-$C_{10}$-alkyl) amides of acrylic acid and of methacrylic acid, e.g. N-ethylacrylamide, N,N-diethylacrylamide, N-butylacrylamide, N-methyl-N-propylacrylamide, N-(n-hexyl)acrylamide, N-(n-octyl)acrylamide and the corresponding methacrylamides, vinylaromatic monomers such as styrene, methylstyrene, vinyltoluene, olefins having 2 to 10 carbon atoms, preferably α-olefins having 3 to 10 carbon atoms, such as propene, 1-butene, 1-pentene, 1-hexene, 1-octene and 1-decene, vinyl esters of aliphatic carboxylic acids such as vinyl acetate, vinyl propionate, vinyl laurate, vinyl nonanoate, vinyl decanoate, vinyl laurate and vinyl stearate, unsaturated nitriles such as acrylonitrile and methacrylonitrile, halogenated olefins such, as vinyl chloride, $C_{11}$-$C_{20}$-alkyl esters of monoethylenically unsaturated monocarboxylic acids having preferably 3 to 6 carbon atoms, e.g. $C_{11}$-$C_{20}$-alkyl acrylates and $C_{11}$-$C_{20}$-alkyl methacrylates such as lauryl acrylate, lauryl methacrylate, isotridecyl acrylate, isotridecyl methacrylate, stearyl acrylate, stearyl methacrylate, di-$C_1$-$C_{20}$-alkyl esters of ethylenically unsaturated dicarboxylic acids having preferably 4 to 8 carbon atoms, e.g. di-$C_1$-$C_{20}$-alkyl esters of fumaric acid and of maleic acid such as dimethyl fumarate, dimethyl maleate, dibutyl fumarate and dibutyl maleate, glycidyl esters of monoethylenically unsaturated monocarboxylic acids having preferably 3 to 6 carbon atoms, such as glycidyl acrylate and glycidyl methacrylate. Preferred further monomers are the esters with $C_1$-$C_{10}$-alkanols of acrylic acid and of methacrylic acid.

In a further embodiment, the linear polymer may be a block polymer comprising a block of polyethylene glycol or of at least one polar ethylenically unsaturated monomer. The molar mass Mn is usually in the range of 200-10 000 g/mol, preferably between 300 and 2000 g/mol, and can be determined by GPC. The block polymer may be of the A-B or A-B-A type, preferably A-B type. The preparation of block polymers of these types is common knowledge. Suitable and preferred polar ethylenically unsaturated monomers are as specified above. Examples of a block of polyethylene glycol are polyethylene glycol or polyethylene glycol monoalkyl ethers having a molar mass Mn of 200 to 10 000 g/mol. Examples of a block of at least one polar ethylenically unsaturated monomer are polyvinylpyrrolidone or poly (meth)acrylic acid or polyethylene glycol monomethyl ether (meth)acrylate. The other block in each case may be formed from polymer blocks from the prior art. The other block is preferably nonpolar; for example, it is formed from caprolactone or propylene oxide. In a further embodiment, the other block comprises polyesters (for example based on a dicarboxylic acid and a diol), polyamide (for example based on a dicarboxylic acid and a diamine), polycarbonate, polyurethane or polyurea. Preferred block polymers are polyethylene glycol-block-polycaprolactone and polyethylene glycol monomethyl ether-block-polycaprolactone and polypropylene glycol-block-polyethylene glycol.

In a further embodiment, the linear polymer may be a polycondensate comprising polyethylene glycol. In the context of the present invention, the term "polycondensate" also include polyaddition products. Examples of polyethylene glycol are polyethylene glycol or polyethylene glycol monoalkyl ethers having a molar mass Mn of 200 to 10 000 g/mol. Examples of polycondensates are polyethers, polyamides, polyimides, polyesters, polycarbonates, polyurethanes and polyureas, preferably polyethers and polyesters. A preferred polycondensate is a polyether based on $C_3$-$C_{24}$ alkylene oxide, particularly propylene oxide, and a polyester based on hydroxycarboxylic acid compounds, dialcohol compounds or diacid compounds, particularly hydroxycarboxylic acid compounds. Preferred hydroxycarboxylic acid compounds are lactones, especially $C_4$ to $C_{18}$-alkyl lactones, most preferably ϵ-caprolactone.

In a further embodiment, the linear polymer may be a polyethylene glycol, in which case the polyethylene glycol is joined to the polycarbonate via a linker. The linker is preferably a polyisocyanate. Examples of polyethylene glycol are polyethylene glycol or polyethylene glycol monoalkyl ethers having a molar mass Mn of 200 to 10 000 g/mol, preferably 300-2000 g/mol. A polyethylene glycol is preferably a polyethylene glycol mono-$C_1$-$C_{18}$-alkyl ether, especially a polyethylene glycol monomethyl ether.

Comb-type polymers are understood here to mean comb polymers which typically comprise relatively long side chains of virtually equal length, preferably aliphatic side chains, at more or less regular intervals on a linear main chain. The molar mass Mn is usually in the range from 500 to 100 000 g/mol and can be determined by GPC. The comb-type polymer preferably comprises polyalkylene glycol mono(meth)acrylate or allyl alcohol alkoxylate (such as polyethylene glycol allyl ether) in polymerized form, preferably polyethylene glycol monoalkyl ether (meth)acrylate with a molar mass Mn of 100 to 5000 g/mol. The polymer more preferably comprises polyethylene glycol monomethyl ether acrylate or polyethylene glycol monomethyl ether methacrylate with a molar mass Mn of in each case 100 to 3000 g/mol, preferably 200 to 1500 g/mol. In addition to polyalkylene glycol mono(meth)acrylate or allyl alcohol alkoxylates, the comb polymer may comprise any desired copolymerizable ethylenically unsaturated monomers. Preferred additional monomers are nonpolar monomers and/or the aforementioned polar ethylenically unsaturated monomers. Preferred nonpolar monomers are $C_1$-$C_{20}$-alkyl(meth) acrylates or vinylaromatics having up to 20 carbon atoms. Examples comprise methyl(meth)acrylate, ethyl(meth)acrylate, n-butyl (meth)acrylate, 2-ethylhexyl(meth)acrylate, lauryl(meth)acrylate or 4-t-butylcyclohexyl (meth)acrylate. Useful vinylaromatic compounds include, for example, vinyltoluene, α-butylstyrene, 4-n-butylstyrene, 4-n-decylstyrene or styrene. Preferred additional monomers are methyl(meth)acrylate, lauryl acrylate, stearyl acrylate, styrene, vinylpyrrolidone or mixtures thereof.

The linear or comb-type polymer can be prepared by commonly known methods (for example from U.S. Pat. No.

5,556,918 and EP-A 742 238). In one embodiment, the linear polymer, which is a homopolymer or random copolymer comprising a polar ethylenically unsaturated monomer, the block polymer comprising a block of polyethylene glycol or based on at least one polar ethylenically unsaturated monomer, and the comb polymer, is prepared by free-radically initiated solution polymerization of the monomers in the presence of an initiator and if appropriate of a regulator. Preference is given to using an initiator which, when it decomposes, forms a hydroxyl radical (OH radical), and/or a regulator which comprises an OH group or an $NH_2$ group. These OH or $NH_2$ groups can be used later as the linker-reactive group.

Suitable initiators are organic hydroperoxides such as tert-butyl hydroperoxide, tetrahydrofuran hydroperoxide, cumene hydroperoxide or 2,2'-azobis(2-methyl-N-(2-hydroxyethyl)propionamide). Suitable regulators are aminoalcohols, aminophenols and especially thioalkanols such as 3-hydroxypropanethiol, 3-mercapto-1,2-propanediol, 2-hydroxyethyl 3-mercaptopropionate, and in particular 2-hydroxyethanethiol (mercaptoethanol). When such a regulator is used, the polymerization can also be performed in the presence of a conventional initiator, for example of a conventional azo initiator or of an organic peroxide such as azobis(isobutyronitrile), di-(tert-butyl) peroxide, didecanoyl peroxide, dibenzoyl peroxide, tert-butyl peracetate or tert-butyl 2-methylperpropionate. When the polymerization is performed in the presence of one of the aforementioned regulators, the regulator will generally be used in an amount of 0.1 to 12% by weight, frequently 0.2 to 8% by weight and especially 0.5 to 5% by weight, based on the total amount of the monomers. Initiators are generally used in an amount of 0.05 to 5% by weight, frequently 0.1 to 4% by weight and more preferably in an amount of 0.2 to 3% by weight, based on the monomers to be polymerized. For further details, reference is made especially to page 3 of EP 742 238, whose disclosure is incorporated by reference.

In a further preferred embodiment, the hyperbranched polycarbonate A1 is joined to at least one functional $C_1$-$C_{24}$ unit comprising an acid group, an amino group or at least two hydroxyl groups. The functional $C_1$-$C_{24}$ unit preferably comprises a carboxylic acid group, a sulfonic acid group, a sulfenic acid group, a sulfinic acid group, a sulfuric ester group (i.e. an organic sulfate), a phosphonic acid group, an amino group or at least two hydroxy-$C_2$-$C_{10}$-alkyl groups, more preferably a carboxylic acid group. Optionally, the functional $C_1$-$C_{24}$ unit may also comprise a plurality of the groups listed at the same time.

In one embodiment, the functional $C_1$-$C_{24}$ unit additionally comprises a joining group with which the functional $C_1$-$C_{24}$ unit can be joined covalently to the hyperbranched polycarbonate, directly or by means of a linker. Suitable joining groups may react with the OH and/or carbonate or carbamoyl chloride groups of the polycarbonate. Examples are carboxylic acids, carboxylic esters, carboxylic anhydrides, isocyanates, amines and alcohols. Further suitable joining groups may react with the linker. Examples are alcohols or amines, preferably alcohols. Suitable linkers are described hereinafter.

The hyperbranched polycarbonate which is linked to the functional $C_1$-$C_{24}$ unit is preferably obtained by reacting the hyperbranched polycarbonate with a functionalizing reagent which comprises the functional $C_1$-$C_{24}$ unit comprising an acid group, an amino group or at least two hydroxyl groups and the joining group, and optionally with a linker.

Suitable functionalizing reagents for direct covalent joining without a linker are anhydrides. Particularly suitable are cyclic carboxylic anhydrides, such as succinic anhydride or phthalic anhydride, especially succinic anhydride. Typically, the anhydrides are reacted with the hyperbranched polycarbonate at elevated temperatures, usually at 80 to 200° C. The reaction can be effected with or without addition of solvents. Further purification is normally not necessary.

Suitable functionalizing reagents for covalent joining by means of a linker are hydroxycarboxylic acids, aminocarboxylic acids, hydroxysulfonic acids, hydroxysulfates, aminosulfonic acids or aminosulfates, hydroxylamines (such as diethanolamine), polyamines (e.g. diethylenetetramine) or polyols (e.g. glycerol, trimethylolpropane, pentaerythritol). Preferred linkers for this purpose are polyisocyanates described below, preferably diisocyanates, more preferably aliphatic diisocyanates (such as hexamethylene diisocyanate and isophorone diisocyanate).

The linear or comb-type polymers are preferably joined to the hyperbranched polycarbonate with the aid of a linker. Usually, the linker is first bonded covalently to the linear or comb-type polymer, in order then to couple the linker-containing polymer onto the hyperbranched polycarbonate. In order that the linker-containing polymer can be prepared, the starting polymer usually comprises a group which can react with the linker (linker-reactive group). The mean number of linker-reactive groups is generally not more than two, and is preferably in the range from 0.3 to 1.8, in particular in the range from 0.5 to 1.5 and especially in the range from 0.6 to 1.4 per polymer molecule. The linker-reactive group may be arranged within the polymer chain or is preferably at the end of the polymer chain.

In the case of a linear polymer which is a homopolymer or random copolymer comprising a polar ethylenically unsaturated monomer, a block polymer comprising a block of polyethylene glycol or based on at least one polar ethylenically unsaturated monomer, or a comb polymer, the linker-reactive group can be introduced as described above by means of a suitable initiator and/or regulator. Alternatively, the linker-reactive group can be introduced at the chain end in a controlled manner by means of a controlled free-radical reaction according to the prior art (such as Atom Transfer Radical Polymerization (ATRP), Reversible Addition Fragmentation Chain Transfer Polymerization (RAFT), or Nitroxide Mediated Polymerization (NMP)). It is equally possible that a functional group in the polymer chain is used as the linker-reactive group, for example one of possibly several OH groups of a polymerized hydroxyethyl (meth) acrylate.

In the case of a polycondensate comprising polyethylene glycol, a linker-reactive group can be obtained at the chain end of the polycondensate by means of a suitable stoichiometry and use of a monofunctional monomer. The linker-reactive group is preferably obtained by ring-opening polymerization of a lactone, such that exactly one functional hydroxyl group forms at the chain end.

In the case of a polyethylene glycol, the linker-reactive group used may be a hydroxyl group at the chain end. Preference is given to polyethylene glycol monoalkyl ethers which have exactly one linker-reactive group at the chain end.

In general, useful linkers include reactive polyfunctional compounds with at least two reactive groups. Preferred linkers are polyisocyanates having a functionality based on the isocyanate groups of at least 1.5, in particular 1.5 to 4.5 and especially 1.8 to 3.5 comprise aliphatic, cycloaliphatic and aromatic di- and polyisocyanates, and the isocyanurates, allophanates, uretdiones and biurets of aliphatic, cycloaliphatic and aromatic diisocyanates. The polyisocyanates preferably have an average of 1.8 to 3.5 isocyanate groups per molecule. Examples of suitable polyisocyanates are aromatic diisocyanates such as toluene 2,4-diisocyanate, toluene 2,6-diisocyanate, commercially available mixtures of toluene 2,4- and 2,6-diisocyanate (TDI), n-phenylene diisocyanate, 3,3'-diphenyl-4,4'-biphenylene diisocyanate, 4,4'-biphenylene diisocyanate, 4,4'-diphenylmethane diisocyanate, 2,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates such as ethylene diisocyanate, ethylidene diisocyanate, propylene 1,2-diisocyanate, 1,6-hexamethylene diisocyanate (HDI), 1,4-tetramethylene diisocyanate, 1,10-decamethylene diisocyanate, and cycloaliphatic diisocyanates such as isophorone diisocyanate (IPDI), cyclohexylene 1,2-diisocyanate, cyclohexylene 1,4-diisocyanate and bis(4,4'-isocyanatocyclohexyl)methane. Among the polyisocyanates, preference is given to those whose isocyanate groups are of different reactivity, such as toluene 2,4-diisocyanate, toluene 2,6-diisocyanate, 2,4'-diphenylmethane diisocyanate, cis- and trans-isophorone diisocyanate, or mixtures of these compounds.

The reaction with the polyisocyanate is effected in the melt or in an organic solvent, preferably in an aprotic polar organic solvent or mixtures of such solvents. Examples are ketones (for example acetone), butyl acetate, tetrahydrofuran (THF), xylene, chlorobenzene, dimethyl sulfoxide (DMSO) or dimethylformamide (DMF). Preferred solvents are butyl acetate, xylene and acetone. The reaction is effected typically at elevated temperatures, the temperature also being guided by the boiling temperature of the solvent selected. The polyisocyanate can be reacted with the first component at 20 to 80° C., but if desired also to 100° C. The further isocyanate group can be reacted at temperatures of 50 to 100° C.

The reaction can be effected in an equimolar manner, which means that the quantitative ratio is selected such that 1 mol of diisocyanate is used per mole of hydroxyl group to be converted in the functionalizing reagent or in the linear or comb-type polymer. Preference is given to working with a slight (e.g. 0 to 15 mol %) excess of the hydroxyl groups, in order to reduce the amount of unconverted diisocyanate. When the free-radical copolymer is OH-functionalized by means of an initiator or regulator, the diisocyanate is reacted in an equimolar amount or in a slight deficiency relative to the OH groups introduced in this way. In the case of symmetric diisocyanates (such as HDI), it may also be advisable to use an excess of diisocyanate and then to remove the excess by distillation.

Preference is given to performing the reaction in the presence of a catalyst. Suitable catalysts are, for example, tertiary amines, for example triethylamine, tri-n-propylamine, N-methylpyrrolidine, N-methylpiperidine and diazabicyclooctane (DABCO), zinc carboxylates, bismuth carboxylates, titanium alkoxides, organotin compounds, especially dialkyltin(IV) salts of aliphatic carboxylic acids such as dibutyltin dilaurate and dibutyltin dioctoate, tin(II) dialkanoates such as tin dioctoate, and cesium salts such as cesium acetate. In one embodiment, zinc carboxylates, bismuth carboxylates, titanium alkoxides are particularly suitable, the carboxylates preferably being $C_1$-$C_{20}$ carboxylates (such as formate, acetate, propionate, hexanoate, octanoate or neodecanoate). The catalyst can be used in amounts of 50 to 50 000 ppm, preferably 100 to 5000 ppm, based on the overall solids.

The reaction is typically performed at elevated temperatures in the range from 40 to 120° C. Which temperature is selected in the individual case depends on the type of organic solvent used. The solvent can subsequently be removed by distillation.

Typically, the reaction will be performed in such a way that the component which is to be functionalized with isocyanate groups (for example the linear or comb-type polymer or the functional $C_1$-$C_{24}$ unit) is first reacted with the diisocyanate in the presence of the catalyst and of a solvent until the isocyanate value in the reaction mixture has fallen by half. In the case of use of a slight hydroxyl group excess, reaction is continued until the theoretical end value corresponds to the complete conversion of the hydroxyl groups. This can be determined, for example, by titrimetric means in a known manner. This is then followed by the addition of the other component (for example hyperbranched polycarbonate). The molar ratio of hyperbranched polycarbonate to linear polymer, comb-type polymer, or to the functional $C_1$-$C_{24}$ unit is 1:1 to 1:25, preferably 1:2 to 1:15. The reaction is continued until the isocyanate value has fallen to zero.

Additionally preferred inventive hyperbranched polymers A are hyperbranched polyesters A2, whose structure and preparation are described in WO 2007/125028.

The hyperbranched polyesters A2 described there are hyperbranched polyesters (a) and reaction products thereof (b), obtainable by (a1) polycondensing at least one dicarboxylic acid or one or more derivatives thereof with one or more at least trifunctional alcohols, or (a2) by polycondensing at least one tricarboxylic acid or higher polycarboxylic acid or one or more derivatives thereof with one or more diols, or (a3) by polycondensing at least one dicarboxylic acid or at least one derivative thereof with a mixture of at least one diol and at least one at least trifunctional alcohol, or (a4) by polycondensing at least one diol with a mixture of at least one dicarboxylic acid or at least one derivative thereof and at least one tricarboxylic or tetracarboxylic acid or at least one derivative thereof, and if appropriate reacting a polyester with at least one isocyanate or chlorocarbonic ester which carries at least one polyalkylene oxide unit attached via a carbonate group, urea group or urethane group.

Preference is also given to hyperbranched polyesters (A2) with an acid number in the range from 1 to 50 mg KOH/g.

Preference is also given to hyperbranched polyesters (A2) in which hyperbranched polyesters (a) are reacted (b1) with at least one reaction product of at least one diisocyanate with a $C_1$-$C_4$-alkyl-capped polyalkylene glycol.

Preference is also given to hyperbranched polymers (A2) in which at least 90 mol % of the functional groups of hyperbranched polyester (a) have been reacted with isocyanate or a chlorocarbonic ester which carries at least one polyalkylene oxide unit attached via a carbonate group, urea group or urethane group.

Additionally preferred are hyperbranched nitrogen-containing polymers A3 from the group of the polyureas, polyurethanes, polyamides, polyesteramides and polyesteramines, whose structure and preparation are described in WO 2006/087227.

Preferred polymers A3 are hyperbranched polyureas, the term "polyurea" in the context of the polymers A3 comprising not just those polymers whose repeat units are joined to one another by urea groups but quite generally polymers obtainable by reacting at least one di- and/or polyisocyanate with at least one compound which has at least one group reactive toward isocyanate groups. These include polymers whose repeat units, as well as urea groups, are also connected by urethane, allophanate, biuret, carbodiimide, amide, uretonimine, uretdione, isocyanurate or oxazolidone (oxazolidinone) groups (see, for example, Kunststofftaschenbuch [Plastics Handbook], Saechtling, 26th ed., p. 491ff Carl-Hanser-Verlag, Munich 1995). The term "polyureas" comprises especially polymers which have urea and/or urethane groups.

The hyperbranched polymers A3 used in accordance with the invention preferably have, as well as urea and/or urethane groups (or further groups arising from the reaction of isocyanate groups), at least four further functional groups. The proportion of functional groups is preferably 4 to 100, more preferably 4 to 30 and especially 4 to 20.

Preference is given to polyureas A3 which have a weight-average molecular weight in the range from about 500 to 100 000, preferably 1000 to 50 000.

Their content of urea and/or urethane groups (and, if present, further groups obtained by reaction of an isocyanate group with a group which is reactive toward it and has an active hydrogen atom) is preferably within a range from 0.5 to 10 mol/kg, more preferably 1 to 10 mol/kg, especially 2 to 8 mol/kg. Useful di- and polyisocyanates include the aliphatic, cycloaliphatic, araliphatic and aromatic di- or polyisocyanates which are known in the prior art and are specified below by way of example. These preferably include 4,4'-diphenylmethane diisocyanate, the mixtures of monomeric diphenylmethane diisocyanates and oligomeric diphenylmethane diisocyanates (polymeric MDI), tetramethylene diisocyanate, tetramethylene diisocyanate trimers, hexamethylene diisocyanate, hexamethylene diisocyanate trimers, isophorone diisocyanate trimer, 4,4'-methylenebis(cyclohexyl) diisocyanate, xylylene diisocyanate, tetramethylxylylene diisocyanate, dodecyl diisocyanate, lysine alkyl ester diisocyanate where alkyl is $C_1$-$C_{10}$-alkyl, 1,4-diisocyanatocyclohexane or 4-isocyanatomethyl-1,8-octamethylene diisocyanate.

Suitable di- or polyisocyanates for forming the polyureas and polyurethanes are more preferably those which have NCO groups of different reactivity. These include 2,4-tolylene diisocyanate (2,4-TDI), 2,4'-diphenylmethane diisocyanate (2,4'-MDI), triisocyanatotoluene, isophorone diisocyanate (IPDI), 2-butyl-2-ethylpentamethylene diisocyanate, 2,2,4- or 2,4,4-trimethyl-1,6-hexamethylene diisocyanate, 2-isocyanatopropylcyclohexyl isocyanate, 3(4)-isocyanatomethyl-1-methylcyclohexyl isocyanate, 1,4-diisocyanato-4-methylpentane, 2,4'-methylenebis(cyclohexyl) diisocyanate and 4-methylcyclohexane 1,3-diisocyanate (H-TDI).

Additionally suitable for forming the polyureas and polyurethanes are isocyanates whose NCO groups at first have equal reactivity, but in which first addition of a reactant onto one NCO group can induce a decline in reactivity in the second NCO group. The examples thereof are isocyanates whose NCO groups are coupled via a delocalized $\pi$ electron system, for example 1,3- and 1,4-phenylene diisocyanate, 1,5-naphthylene diisocyanate, diphenyl diisocyanate, toluidine diisocyanate or 2,6-tolylene diisocyanate.

In addition, it is possible to use, for example, oligo- or polyisocyanates which can be prepared from the abovementioned di- or polyisocyanates or mixtures thereof by joining by means of urea, allophanate, urethane, biuret, uretdione, amide, isocyanurate, carbodiimide, uretonimine, oxadiazinetrione or iminooxadiazinedione structures.

The compounds having at least two isocyanate-reactive groups used are preferably di-, tri- or tetrafunctional compounds whose functional groups have a different reactivity toward NCO groups.

For the preparation of polyureas, preference is given to using isocyanate-reactive products which have at least two amino groups in the molecule.

These are, for example, ethylenediamine, N-alkylethylenediamine, propylenediamine, N-alkylpropylenediamine, hexamethylenediamine, N-alkylhexamethylenediamine, diaminodicyclohexylmethane, phenylenediamine, isophoronediamine, amine-terminated polyoxyalkylenepolyols (so-called Jeffamines), bis(aminoethyl)amine, bis(aminopropyl)amine, bis(aminohexyl)amine, tris(aminoethyl)amine, tris(aminopropyl)amine, tris(aminohexyl)amine, trisaminohexane, 4-aminomethyl-1,8-octamethylenediamine, N'-(3-aminopropyl)-N,N-dimethyl-1,3-propanediamine, trisaminononane or melamine. In addition, mixtures of the compounds mentioned are also usable.

Preferred compounds for preparing polyurethanes and polyurea-polyurethanes are those having at least one primary and at least one secondary hydroxyl group, at least one hydroxyl group and at least one mercapto group, more preferably having at least one hydroxyl group and at least one amino group, in the molecule, especially aminoalcohols, aminodiols and aminotriols, since the reactivity of the amino group compared to the hydroxyl group in the reaction with isocyanate is significantly higher. Examples of the compounds having at least two isocyanate-reactive groups mentioned are propylene glycol, glycerol, mercaptoethanol, ethanolamine, N-methylethanolamine, diethanolamine, ethanolpropanolamine, dipropanolamine, diisopropanolamine, 2-amino-1,3-propanediol, 2-amino-2-methyl-1,3-propanediol or tris(hydroxymethyl)aminomethane. In addition, mixtures of the compounds mentioned are also usable.

Hyperbranched polyurethanes and polyureas with chain-extended branches can be obtained, for example, by using, for the polymerization reaction, as well as the $AB_x$ molecules, additionally a diisocyanate and a compound which has two groups reactive with isocyanate groups in a molar ratio of 1:1. These additional AA and BB compounds may also possess further functional groups which, however, must not be reactive toward the A or B groups under the reaction conditions. In this manner, further functionalities can be introduced into the hyperbranched polymer.

Group B1

Vinylpyrrolidone copolymers B1 and the preparation thereof are described in WO 99/27916, WO 2007/017452 and WO 2008/064990.

If appropriate, the copolymers B1 may comprise 0 to 39% by weight, preferably 0 to 10% by weight, of at least one further free-radically copolymerizable monomer B3), where the percentages by weight of the individual components a) to c) add up to 100% by weight.

A preferred monomer B1-1 is 1-vinylpyrrolidone.

The proportion of the monomers B1-1 in the copolymer is preferably in the range from 70 to 95% by weight, more preferably in the range of 75 to 90% by weight.

Useful Monomers B1-2 Include:

N—$C_8$-$C_{30}$-alkyl- or N,N—$C_8$-$C_{30}$-dialkyl-substituted amides of monoethylenically unsaturated $C_3$-$C_8$-carboxylic acids, where the alkyl radicals are straight-chain or branched aliphatic or cycloaliphatic alkyl radicals having 8 to 30, preferably 8 to 18 carbon atoms. Useful examples among the monoethylenically unsaturated carboxylic acids having 3 to 8 carbon atoms in this context include acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid and itaconic acid, preferably acrylic acid, methacrylic acid, maleic acid or mixtures of the carboxylic acids mentioned.

Preferred amidated comonomers are, for example, N-stearylacrylamide, N-stearylmethacrylamide, N-(1-methyl)undecylacrylamide, N-(1-methyl)undecylmethacrylamide, N-dodecylacrylamide, N-dodecylmethacrylamide, N-octylacrylamide, N-octylmethacrylamide, N,N-dioctylacrylamide, N,N-dioctylmethacrylamide, N-cetylacrylamide, N-cetylmethacrylamide, N-myristylacrylamide, N-myristylmethacrylamide, N-(2-ethyl)hexylacrylamide, N-(2-ethyl)hexylmethacrylamide.

In the case of maleic anhydride as a comonomer, it can be reacted in a polymer-analogous manner with N-alkylamines by ring opening to give the corresponding amides.

The further comonomers B1-2 used may be monoethylenically unsaturated $C_3$-$C_8$-carboxylic esters with a $C_8$-$C_{30}$-alcohol, preferably a $C_3$-$C_{18}$-alcohol.

Of particular significance in this context are the acrylic or methacrylic esters with fatty alcohols of chain length from 8 to 18 carbon atoms, where the alkyl radicals may be branched or unbranched.

These include in particular: octyl acrylate, 2-ethylhexyl acrylate, nonyl acrylate, decyl acrylate, lauryl acrylate, myristyl acrylate, cetyl acrylate, stearyl acrylate, oleyl acrylate, behenyl acrylate, octyl methacrylate, 2-ethylhexyl methacrylate, nonyl methacrylate, decyl methacrylate, lauryl methacrylate, myristyl methacrylate, cetyl methacrylate, stearyl methacrylate, oleyl methacrylate, behenyl methacrylate, tert-butylcyclohexyl acrylate.

As a further component B1-2, it is possible to use vinyl esters of long-chain aliphatic, saturated or unsaturated, unbranched $C_8$-$C_{30}$-carboxylic acids such as caprylic acid, capric acid, neodecanoic acid (2,2,3,5-tetramethylhexanoic acid), lauric acid, myristic acid, palmitic acid, stearic acid, arachic acid, behenic acid, lignoceric acid, cerotic acid and melissic acid.

In addition, monomers B1-2 which may be copolymerized include $C_8$-$C_{30}$-alkyl vinyl ethers, preferably $C_8$-$C_{18}$-alkyl vinyl ethers. Preferred alkyl radicals of the vinyl ethers include branched or unbranched $C_8$-$C_{18}$-alkyl chains, for example n-octyl, 2-ethylhexyl, n-nonyl, n-decyl, n-undecyl, n-dodecyl, n-tridecyl, n-tetradecyl, n-pentadecyl, n-hexadecyl, n-heptadecyl and n-octadecyl.

Particularly preferred monomers B1-2 are lauryl acrylate, myristyl acrylate and vinyl neodecanoate.

The proportion of monomers b) is preferably 1 to 25 and most preferably 5 to 15% by weight.

Useful additional free-radically copolymerizable monomers B1-3 include:

monoethylenically unsaturated carboxylic and sulfonic acids having 3 to 8 carbon atoms or salts thereof, such as acrylic acid, methacrylic acid, dimethacrylic acid, ethacrylic acid, maleic acid, citraconic acid, methylenemalonic acid, allylacetic acid, crotonic acid, fumaric acid, mesaconic acid and itaconic acid, and acrylamido-2-methyl-1-propanesulfonic acid (AMPS).

From this group of monomers, preference is given to using acrylic acid, methacrylic acid, AMPS or mixtures of the acids mentioned.

The monoethylenically unsaturated acids can be used in the copolymerization in the form of the free acid, in the form of anhydrides or else in partially or fully neutralized form. Preference is given to sodium and ammonium salts.

Preferred copolymers B1 comprise at least one further copolymerizable monomer B1-3, preferably in a proportion of up to 10% by weight (based on the overall copolymer).

Additionally preferred copolymers B1 comprise 1 to 40% by weight of component B1-2.

Additionally preferred copolymers B1 comprise lauryl acrylate and/or myristyl acrylate as component B1-2, especially vinylpyrrolidone as component B1-1 and lauryl acrylate and/or myristyl acrylate as component B1-2.

Additionally preferred vinylpyrrolidone copolymers B1 comprise vinyl neodecanoate as component B1-2, especially vinylpyrrolidone as component B1-1 and vinyl neodecanoate as component B1-2.

Group B2

Polyvinyllactam-polyvinyl acetate block copolymers B2 and preparation thereof are described in WO 2008/058848.

Preference is given to copolymers B2 in which the polyvinyllactam block is a polyvinylpyrrolidone.

Additionally preferred are copolymers B2 which have number-average molecular weights Mn of 1000 to 50 000, especially of 1000 to 30 000.

Additionally preferred are copolymers B2 in which the polyvinyllactam-polyvinyl acetate block copolymers have an A-B, A-B-A or B-A-B structure.

Additionally preferred are copolymers B2 which are water-soluble.

Group B3

The vinyllactam copolymers of group B3 are known and are described with their preparation in WO 2007/065 845.

Preference is given to preparing the copolymers B3 by free-radically initiated copolymerization of N-vinyllactams with monoolefinically unsaturated comonomers which bear hydroxyl or amino groups or comprise a group convertible by hydrolysis to hydroxyl or amino groups, and then coupling the polyalkylene oxide side chains onto the amino or hydroxyl groups of the vinyllactam copolymers.

Preference is given to copolymers B3 which comprise, as monoolefinically unsaturated comonomers, monomers from the group consisting of vinyl esters of $C_2$-$C_8$-carboxylic acids, monovinyl ethers of $C_2$-$C_8$-diols, vinylamides, hydroxyalkyl and aminoalkyl esters of acrylic acid and of methacrylic acid.

Preference is further given to copolymers B3 which are obtained by free-radically initiated copolymerization of N-vinyllactams and vinyl acetate with subsequent hydrolysis of the ester groups.

Preference is further given to copolymers B3 which comprise N-vinylpyrrolidone as the N-vinyllactam.

Preference is further given to copolymers B3 which are obtained by reaction of 50 to 99.9 mol % of N-vinyllactams and 0.1 to 50 mol % of comonomers.

Preference is further given to copolymers B3 which are obtained by reaction of 80 to 99 mol % of N-vinyllactams and 1 to 20 mol % of comonomers.

Preference is further given to copolymers B3 which have molecular weights of 1000 to 50 000.

Preference is further given to copolymers B3 in which the polyalkylene oxides are selected from the group consisting of polyethylene glycols, polypropylene glycols, polybutylene glycols and the monoalkoxylated derivatives thereof, the term "monoalkoxylated derivatives" not comprising any aralkyl monoethers.

Preference is further given to copolymers B3 which comprise polyoxyethylene-polyoxypropylene block copolymers as polyalkylene oxides.

Preference is further given to copolymers B3 in which the coupling of the polyalkylene oxide side chains is via diisocyanates.

Preference is further given to copolymers B3 in which the polyalkylene oxides are functionalized by reaction with a diisocyanate before the reaction with the vinyllactam copolymer.

Preference is further given to copolymers B3 in which the polyalkylene oxides are used in equimolar amounts based on the amino or hydroxyl groups of the vinyllactam copolymer.

Preference is further given to copolymers B3 in which the diisocyanate used is isophorone diisocyanate.

Preference is further given to copolymers B3 in which the coupling of the polyalkylene oxide side chains is by direct alkoxylation with alkylene oxides.

Preference is further given to copolymers B3 which have molecular weights $M_w$ of 1000 to 50 000 g/mol.

Group B4

N-Vinyllactam copolymers B4 and preparation thereof are described in WO 2008/064987.

Preference is given to copolymers B4 comprising, especially consisting of, 90-10% by weight of component B4-1 and 10-40% by weight of component B4-2.

Additionally preferred are copolymers B4 in which component B4-2 comprises 2-vinylpyridine, 3-vinylpyridine, 4-vinylpyridine or 2-vinyl-5-methylpyridine.

Particular preference is given to copolymers B4 in which component B4-1 comprises 1-vinyl-2-pyrrolidone.

Equally preferred are copolymers B4 which comprise 1-vinyl-2-pyrrolidone as component B4-1 and 4-vinylpyridine as component B4-2, and especially consist of these components.

Group B5

The copolymers B5 and preparation thereof are described in WO 2006/018135.

Preference is further given to copolymers B5 obtainable by polymerizing

B5-1 to 50 mol % of at least one monomer A
B5-2 50 to 99 mol % of at least one monomer B
B5-3 0 to 5 mol % of one or more different difunctional crosslinker components and
B5-4 0 to 4 mol % of one or more different regulators and
B5-5 0 to 49 mol % of at least one monomer C
where the molar percentages of the individual components must add up to 100 mol %.

Additionally preferred are copolymers B5 obtainable by polymerizing

B5-1 1 to 30 mol % of at least one monomer A
B5-2 50 to 99 mol % of at least one monomer B
B5-3 0 to 3 mol % of one or more different difunctional crosslinker components and
B5-4 0 to 3 mol % of one or more different regulators and
B5-5 0 to 49 mol % of at least one monomer C
where the molar percentages of the individual components must add up to 100 mol %.

Additionally preferred are copolymers B5 obtainable by polymerizing

B5-1 1 to 30 mol % of at least one monomer A
B5-2 50 to 99 mol % of at least one monomer B
B5-3 0 to 3 mol % of one or more different difunctional crosslinker components and
B5-4 0 to 3 mol % of one or more different regulators and
B5-5 0 to 49 mol % of at least one monomer C
where the molar percentages of the individual components must add up to 100 mol %.

Additionally preferred are copolymers B5 in which the at least one monomer A is selected from the group of monomers B5-1 where $R^3$ and $R^4$ are each H, $R^5$ is phenyl and n is an integer from 1 to 10.

Additionally preferred are copolymers B5 in which the at least one monomer B is selected from the group of N-vinylpyrrolidone and N-vinylcaprolactam, especially N-vinylpyrrolidone.

Group C

The copolymers based on diisocyanates F and preparation thereof are described in WO 2008/065050.

Preference is given to copolymers F in which $R^c$ is a compound of the formula (IVa)

$$R^6—O—(C_2H_4O)_z— \quad \text{(IVa)}$$

in which $R^6$ is $H_x$ or unbranched or branched, saturated or unsaturated $C_1$-$C_{40}$-alkyl and z is an integer from 1 to 100, preferably 5 to 100.

Preference is further given to copolymers C in which $R^b$ is derived from 1,4-butylene diisocyanate, 1,6-hexamethylene diisocyanate (HDI), isophorone diisocyanate (IPDI), 2,2,4- and/or 2,4,4-trimethylhexamethylene diisocyanate, isomeric bis(4,4'-isocyanatocyclohexyl)methanes or mixtures thereof with any desired isomer content, 1,4-cyclohexylene diisocyanate, 4-isocyanatomethyl-1,8-octane diisocyanate (nonane triisocyanate), alkyl 2,6-diisocyanatohexanoates (lysine diisocyanates) having $C_1$-$C_8$-alkyl groups, toluene 2,4-diisocyanate (TDI), toluene 2,6-diisocyanate (TDI) or mixtures thereof, 4,4-diphenylmethane diisocyanate (MDI), 2,4'-diphenylmethane diisocyanate, 2,2'-diphenylmethane diisocyanate, 1,5-naphthylene diisocyanate (NDI) and/or 1,4-phenylene diisocyanate (PDI), especially from toluene diisocyanate or isophorone diisocyanate. Additionally preferred are copolymers C in which $R^a$ is branched or unbranched $C_6$-$C_{24}$-alkyl, $C_3$-$C_8$-cycloalkyl, phenyl, $C_1$-$C_3$-alkyl-substituted phenyl, benzyl, $C_4$-$C_6$-alkyl substituted by $C_4$-$C_{12}$-alkoxy, or $C_1$-$C_4$-alkyl substituted by di($C_1$-$C_4$-alkyl)amino.

Group D

The copolymers D based on ethylenically unsaturated dicarboxylic mono- and diesters and preparation thereof are described in WO 2008/064986.

Preference is given to copolymers D in which, in the alcohol group (IV) of component D2, n is 0-50 and p is 1-60.

Preference is further given to copolymers D in which $R^{11}$ is a phenyl group substituted by 1, 2, 3 or 4 identical or different $C_1$-$C_{20}$-alkyl groups, especially nonylphenyl.

Additionally preferred are copolymers D in which component D2 is a mono- or diester of an unsaturated dicarboxylic acid having 4 to 8 carbon atoms, especially a maleic mono- or diester.

Group E

N-Vinylamide copolymers E and preparation thereof are described in WO 2008/064987.

Preference is given to copolymers E comprising, especially consisting of, 90-10% by weight of component E1 and 10-40% by weight of component E2.

Additionally preferred are copolymers E in which component E2 comprises 2-vinylpyridine, 3-vinylpyridine, 4-vinylpyridine or 2-vinyl-5-methylpyridine.

Equally preferred are copolymers E which comprise vinylacetamide as component E1 and 4-vinylpyridine as component E2, and especially consist of these components.

Group F

Comb polymers F and preparation thereof are described in WO 2008/040786.

Preference is given to comb polymers F in which at least 50% by weight of the repeat units forming the poly($C_2$-$C_4$-alkylene ether)ols have the formula $CH_2CH_2O$.

Additionally preferred are comb polymers F in which the poly($C_2$-$C_4$-alkylene ether)ols have a molecular weight in the range from 200 to 2000.

Additionally preferred are comb polymers F in which the poly($C_2$-$C_4$-alkylene ether)ol is a poly-$C_2$-$C_4$-alkylene glycol mono-$C_1$-$C_{10}$-alkyl ether.

Additionally preferred are comb polymers F in which the at least one monomer Mb is selected from esters of monoethylenically unsaturated $C_3$-$C_8$-monocarboxylic acids with poly($C_2$-$C_4$-alkylene ether)ols, especially from esters of acrylic acid and of methacrylic acid with poly($C_2$-$C_4$-alkylene ether)ols.

Additionally preferred are comb polymers F in which the at least one monomer Ma is selected from esters of acrylic acid and of methacrylic acid with $C_1$-$C_{20}$-alkanols, $C_5$-$C_{10}$-cycloalkanols, phenyl-$C_1$-$C_4$-alkanols or phenoxy-$C_1$-$C_4$-alkanols.

Additionally preferred are comb polymers F in which the at least one monomer Mb accounts for 10 to 90% by weight based on the total amount of monomers M.

Additionally preferred are comb polymers F in which the at least one monomer Ma accounts for 10 to 90% by weight based on the total amount of monomers M.

Additionally preferred are comb polymers F in which the monomers M additionally comprise one or more monomers Mc with a water solubility greater than 60 g/l at 20° C.

Additionally preferred are comb polymers F in which the monomer Mc is selected from monoethylenically unsaturated $C_3$-$C_8$-monocarboxylic acids and monoethylenically unsaturated $C_4$-$C_8$-dicarboxylic acids.

Additionally preferred are comb polymers F in which the monomer Mc accounts for 5 to 40% by weight based on the total amount of monomers M.

Additionally preferred are comb polymers F which have a number-average molecular weight in the range from 1000 to 500 000.

Group G

Copolymers G and preparation thereof are described in EP-A 0 947 243.

Preference is given to copolymers G in which the N-vinylcarboxamide of the formula (VIII) is N-vinylformamide or N-vinyl-N-methylacetamide.

Additionally preferred are copolymers G in which the monomers G 21 and G 22 are selected from compounds of the formula (VIII)

(VIII)

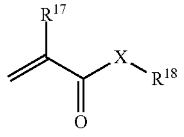

in which $R^{17}$ is a hydrogen atom or a methyl group, $R^{18}$ is $C_8$-$C_{30}$-alkyl, $C_8$-$C_{30}$-cycloalkyl or $C_8$-$C_{30}$-alkenyl, X is O or $NR^{19}$ and $R^{19}$ is H or $C_1$-$C_{30}$-alkyl.

Additionally preferred are copolymers G in which the further copolymerizable monomer is selected from G 31 monoethylenically unsaturated $C_3$-$C_8$-carboxylic acids;

G 32 esters of monoethylenically unsaturated $C_3$-$C_8$-carboxylic acids with aliphatic or cycloaliphatic $C_1$-$C_7$-alcohols, $C_1$-$C_4$-diols, mono- or di-$C_1$-$C_4$-alkylamino $C_1$-$C_4$-alcohols;

G 33 amides of monoethylenically unsaturated $C_3$-$C_8$-carboxylic acids, mono- or di-$C_1$-$C_7$-alkyl amides of monoethylenically unsaturated $C_3$-$C_8$-carboxylic acids;

G 34 nitriles of monoethylenically unsaturated $C_3$-$C_8$-carboxylic acids;

G 35 N-vinyllactams and N-vinylimidazoles;

G 36 monoethylenically unsaturated compounds with sulfonic acid groups;

G 37 monoethylenically unsaturated compounds with phosphonic acid groups;

G 38 vinyl esters of aliphatic or cycloaliphatic $C_1$-$C_7$-carboxylic acids;

G 39 vinyl ethers of aliphatic and cycloaliphatic $C_1$-$C_7$-alcohols;

G 310 vinylaromatics;

G 311 acrylamidoglycolic acid or diallylammonium chloride.

Additionally preferred are copolymers G in which the further copolymerizable monomer is selected from acrylic acid, methacrylic acid, maleic acid, N-vinylpyrrolidone and N-vinylcaprolactam.

Additionally preferred are copolymers G of

G1 vinylformamide and/or N-vinyl-N-methylacetamide;

G2 at least one (meth)acrylic ester of fatty alcohols having 12 to 24 carbon atoms and/or vinyl esters of fatty acids having 8 to 18 carbon atoms; and G3 optionally acrylic acid, methacrylic acid, maleic acid, vinylpyrrolidone or N-vinylcaprolactam.

Group H

The copolymers H and preparation thereof are described in WO 03/055944.

Preference is given to copolymers H in which the comonomer H1 comprises the sodium and/or ammonium salts of acrylamidopropylmethylenesulfonic acid (AMPS).

Additionally preferred are copolymers H1 in which the macromonomers H2 are those of the formula (IX)

$$R^{20}—Y—(R^{21}—O)_x(R^{23}—O)_z—R^{22} \quad (IX)$$

in which $R^{20}$ is a vinyl, allyl, acryloyl, methacryloyl, senecioyl or crotonyl radical;

$R^{21}$ and $R^{23}$ are each independently ($C_2$-$C_4$)-alkylene, x and z are each independently an integer from 0 to 500, preferably where x+z is greater than or equal to 1;

Y is O, S, PH or NH, preferably O; and $R^{22}$ is hydrogen or a saturated or unsaturated, linear or branched, aliphatic, cycloaliphatic or aromatic ($C_1$-$C_{100}$)-hydrocarbon radical, preferably ($C_1$-$C_{30}$)-hydrocarbon radical.

Additionally preferred are copolymers H in which $R^{20}$ is an acryloyl or methacryloyl radical;

$R^{21}$ and $R^{23}$ are each independently $C_2$-alkylene or $C_3$-alkylene;

x and z are each independently an integer from 0 to 50, preferably where x+z is greater than or equal to 1;

$R^{22}$ is an aliphatic ($C_4$-$C_{22}$)-alkyl or -alkenyl radical, preferably ($C_{10}$-$C_{22}$)-alkyl or -alkenyl radical;

a phenyl radical;

a ($C_1$-$C_{22}$)-alkylphenyl radical, preferably (sec-butyl)- and (n-butyl)alkylphenyl radical;

a poly(($C_1$-$C_{22}$)alkyl)phenyl radical, preferably tris(sec-butyl)phenyl radical and tris(n-butyl)phenyl radical, or a polystyrylphenyl radical, preferably tristyrylphenyl radical.

Additionally preferred are copolymers H in which the $R^{16}$ radical is a 2,4,6-tris(sec-butyl)phenyl radical or 2,4,6-tris(1-phenylethyl)phenyl radical.

Additionally preferred are copolymers H obtainable by free-radical copolymerization of H1. acrylamidopropylmethylenesulfonic acid (AMPS), the sodium salt of acrylamidopropylmethylenesulfonic acid (AMPS) and/or the ammonium salt of acrylamidopropylmethylenesulfonic acid, preferably the ammonium salt of acrylamidopropylmethylenesulfonic acid (AMPS);

H2. one or more macromonomers selected from the group of the esters formed from methacrylic or acrylic acid, preferably methacrylic acid, and compounds of the formula (X)

$$HO—(CH_2—CH_2—O)_x—R^{22} \quad (X)$$

in which x is from 0 to 50, preferably from 1 to 50, more preferably from 5 to 30, and $R^{22}$ is a ($C_{10}$-$C_{22}$)-alkyl radical, and H3. optionally one or more comonomers selected from the group of acrylamide, vinylformamide, N-vinylmethylacetamide, sodium methallylsulfonate, hydroxyethyl methacrylate, acrylic acid, methacrylic acid, maleic anhydride, methacrylamide, vinyl acetate, N-vinylpyrrolidone, vinylphosphonic acid, styrene, styrenesulfonic acid (sodium salt), t-butyl acrylate and methyl methacrylate.

Additionally preferred are copolymers H in which the macromonomers K2 are esters formed from acrylic or methacrylic acid and alkyl ethoxylates selected from the group of the ($C_{10}$-$C_{18}$)-fatty alcohol polyglycol ethers with 8 EO units;
$C_{11}$-oxo alcohol polyglycol ethers with 8 EO units,
($C_{12}$-$C_{14}$)-fatty alcohol polyglycol ethers with 7 EO units,
($C_{12}$-$C_{14}$)-fatty alcohol polyglycol ethers with 11 EO units,
($C_{16}$-$C_{18}$)-fatty alcohol polyglycol ethers with 8 EO units,
($C_{16}$-$C_{18}$)-fatty alcohol polyglycol ethers with 15 EO units,
($C_{16}$-$C_{18}$)-fatty alcohol polyglycol ethers with 11 EO units,
($C_{16}$-$C_{18}$)-fatty alcohol polyglycol ethers with 20 EO units,
($C_{16}$-$C_{18}$)-fatty alcohol polyglycol ethers with 25 EO units,
($C_{18}$-$C_{22}$)-fatty alcohol polyglycol ethers with 25 EO units,
iso-($C_{16}$-$C_{18}$)-fatty alcohol polyglycol ethers with 25 EO units and/or
$C_{22}$-fatty alcohol polyglycol ethers with 25 EO units.

Additionally preferred are copolymers H in which the number-average molecular weight of the polymers is 1000 to 20 000 000 g/mol, preferably 10 000 to 5 000 000 g/mol, especially preferably 15 000 to 1 500 000 g/mol.

Additionally preferred are crosslinked copolymers H.

Preference is given to the use of solubilizers of group A, especially A1, A2 and/or A3.

Preference is also given to the use of solubilizers of group B.

Preference is also given to the use of solubilizers of group B1.

Preference is also given to the use of solubilizers of group B2.

Preference is also given to the use of solubilizers of group B3.

Preference is also given to the use of solubilizers of group B4.

Preference is also given to the use of solubilizers of group B5.

Preference is also given to the use of solubilizers of group C.

Preference is also given to the use of solubilizers of group D.

Preference is also given to the use of solubilizers of group E.

Preference is also given to the use of solubilizers of group F.

Preference is also given to the use of solubilizers of group G.

Preference is also given to the use of solubilizers of group H.

Particular preference is given to the use of solubilizers of groups A, especially A1, B, especially B1, B2, B3 and/or B5. Further particular preference is given to the use of solubilizers of group A, especially A1 and/or B1.

Very particular preference is given to the use of solubilizers A, especially A1.

Preference is given to the use of one (1) solubilizer.

Preference is also given to the use of a mixture of two or more solubilizers, especially 2, 3 or 4 solubilizers. Preference is given to solubilizer mixtures which comprise only solubilizers from one (1) of groups A to H. Preference is also given to solubilizer mixtures which comprise two or more solubilizers from two or more of groups A to H.

The (weight) ratio of active ingredient(s) and solubilizer(s) is preferably from 1:1 to 1:200, more preferably from 1:1 to 1:20, most preferably from 1:1 to 1:10.

Preference is given in accordance with the invention to the use of a formulation in which active ingredient(s) and solubilizer(s) are present in concentrated form, which is diluted with water for application, preference being given to a dilution factor of 1:5000 to 1:10, especially of 1:1000 to 1:50.

These concentrates preferably comprise 1 to 75% by weight (based on the overall concentrate) of the mixture of active ingredient(s) and solubilizer(s).

It is also possible to correspondingly dilute a formulation of the active ingredient and then to add solubilizer, or to dilute this formulation with water which comprises the solubilizer.

In one embodiment of the invention, as well as active ingredient(s) (a) and solubilizer(s) (b), one or more adjuvants (c) are used. Preference is given firstly to the adjuvants described in WO 03/053345, i.e. one or more substances from the groups of Z1 tristyrylalkyl ether sulfates or phosphates, such as 2,4,6-tris[1-(phenyl)ethyl]phenyl-omega-hydroxy-poly(oxyethylene)sulfate, which are available, for example, as Soprohor® 4D-384, Soprophor® 30-33, Soprophor® BSU and Soprophor® 796IP from Rhodia;

Z2 nonionic surfactants based on perfluoroalkyl ethoxylate (for example obtainable as Fluowet® OTV from Clariant);

Z3 a mixture of 83% highly refined petroleum oil based on paraffin and 17% alkylarylpolyoxyethylene glycols (obtainable as Drexel Activate Oil from Drexel Chemical Company);

Z4 polyethers or organomodified tri- and polysiloxanes, such as modified polysiloxane polyethers, for example obtainable as Break Thru® S240 from Evonik or Silwet L-77 from Momentive;

Z5 a nonionic surfactant mixture of alkyloxypolyethyleneoxyethanols of the formula $CH_3CH[(CH_2)_nCH_3][O$ $(C_2H_4O)_mH]$ where n=9-15 and m=3-40 (obtainable as SM-9® from Safe Materials, Inc.)

Z6 a silicone surfactant mixture of 100% 2-(3-hydroxypropyl)heptamethyltrisiloxane, ethoxylated acetate, allyloxypolyethylene glycol monoallylacetate and polyethylene glycol diacetate (obtainable as Sylgard® 309 from Wilber-Ellis-Company);

Z7 a biodegradable, low-foaming nonionic surfactant comprising primary alkyl polyoxyethylene ethers, free fatty acids and adjuvants (obtainable as Aktivator 90® from Laveland Industries, Inc.);

Z8 a nonionic surfactant mixture of fatty acid and alcohol ethoxylates based on soybeans (obtainable as Preference® NIS from Cenex/Lan O'Lakes Agronomy Company);

Z9 an anionic surfactant mixture comprising 58% ammonium n-alcohol ether sulfate (obtainable as Rhodapex® CO-436 from Rhodia);

Z10 an anionic surfactant mixture comprising 58% ammonium nonylphenol ether sulfate (obtainable as Rhodapex® CE-128 from Rhodia);

Z11 a mixture of polyalkylene oxide-modified polydimethylsiloxane and nonionic surfactants (obtainable as Thoroughbred® from Estes Inc.) and Z12 a nonionic detergent composed of 100% polyoxyethylene (10)-isooctyl cyclohexyl ether (obtainable as Triton® x-100 from Aldrich Chemical Company).

Additionally preferred as adjuvants (c) are compounds from group Z13:

Z13 alkoxylated fatty alcohols and/or fatty acids, which may additionally each be etherified, sulfonated or phosphonated, for example obtainable as Genapol® XM 100 or Genapol® 060 from Clariant, or as Alkamul® B or Alkamul® A from Rhodia.

Preference is given to adjuvants of groups Z1, Z4 and Z13, especially Z1 and Z4.

In one embodiment of the invention, one or more adjuvants of groups Z1 to Z14 are used. In a further embodiment of the invention, no adjuvants of groups Z1-Z13, preferably of groups Z1 to Z12, are used.

If adjuvants of groups Z1-Z13 are used, they can be added to the concentrate or else only to the application liquor. The addition to the application liquor may, for example, be simultaneous with that of the solubilizer.

The amount of adjuvants Z1-Z13—if used—is preferably at least half, more preferably exactly the same as, the amount of active ingredient in g used, and not more than up to fifty times, preferably twenty-five times and more preferably not more than twenty times the amount of active ingredient in g used.

As well as active ingredients (a), solubilizer(s) (b) and if appropriate adjuvants (c), the active ingredient compositions (i.e. the formulations and the aqueous application forms obtainable by dilution) may comprise, as component (d), customary formulation aids in the amounts customary therefor.

These include, for example, rheology modifiers (thickeners), antifoams, bactericides, antifreezes, pH controllers, stabilizers and plasticizers.

Suitable thickeners are compounds which impart pseudoplastic flow behavior to aqueous compositions, i.e. high viscosity at rest and low viscosity in the agitated state. Examples here include polysaccharides such as xanthan (Keizan® from Kelco; Rhodopol® 23 from Rhone Poulenc; or Veegum® from R.T. Vanderbilt), and inorganic layer minerals such as Attaclay® (from Engelhardt) or Van Gel B (from R.T. Vanderbilt).

Suitable stabilizers may be low molecular weight components, for example mono- and diglycerides, esters of the monoglycerides, alkylglucosides, lecithin, fatty acid derivatives of urea and urethanes.

Suitable plasticizers are sucrose, glucose, lactose, fructose, sorbitol, mannitol or glycerol.

Examples of useful antifoams suitable for the inventive compositions include silicone emulsions (for example Silicon® SRE, from Wacker, or Rhodorsil® from Rhodia), long-chain alcohols, fatty acids and mixtures thereof.

Bactericides can be added to the inventive compositions for stabilization against infestation with microorganisms. They are typically isothiazolone compounds, e.g. 1,2-benzisothiazolin-3-one, 5-chloro-2-methylisothiazol-3-one, 2-methylisothiazol-3-one or 2-octylisothiazol-3-one, which are available, for example, under the tradenames Proxel® from Arch Chemical Inc., Acticide® RS from Thor Chemie and Kathon® MK from Rohm & Haas.

Suitable antifreezes are organic polyols, e.g. ethylene glycol, propylene glycol or glycerol. These are used in aqueous formulations, typically in amounts of not more than 20% by weight, for example 1 to 20% by weight and especially 2 to 10% by weight, based on the total weight of the aqueous active ingredient formulation.

If appropriate, the active ingredient compositions may comprise 0.1 to 5% by weight, based on the total amount of the formulation prepared, of pH regulators for regulating the pH of the formulation or of the diluted application form, the amount and type of the regulator used being guided by the chemical properties and the amount of the active ingredients and solubilizers. Examples of buffers are alkali metal salts of weak inorganic or organic acids, for example phosphoric acid, boric acid, acetic acid, propionic acid, citric acid, fumaric acid, tartaric acid, oxalic acid and succinic acid.

Examples of conventional surfactants are the nonionic, anionic, cationic or zwitterionic emulsifiers, wetting agents or dispersants specified hereinafter, for example the nonionic substances of groups b1) to b15)

b1) aliphatic $C_8$-$C_{30}$-alcohols which may be alkoxylated, for example, with 1-60 alkylene oxide units, preferably 1-60 EO and/or 1-30 PO and/or 1-15 BO in any desired sequence. In this context, EO represents a repeat unit derived from ethylene oxide, PO one derived from propylene oxide, and BO one derived from butylene oxide. The terminal hydroxyl groups of these compounds may be end group-capped by an alkyl, cycloalkyl or acyl radical having 1-24 and especially 1 to 4 carbon atoms. Examples of such compounds are: Genapol®C, L, 0, T, UD, UDD, X products from Clariant, Plurafac® and Lutensol®A, AT, ON, TO, M products from BASF SE, Marlipal®24 and 013 products from Condea, Dehypon® products from Henkel, Ethylan® products from Akzo-Nobel such as Ethylan CD 120;

b2) copolymers consisting of EO, PO and/or BO units, especially EO/PO block copolymers such as the Pluronic® products from BASF SE and the Synperonic® products from Uniqema with a molecular weight of 400 to $10^6$ daltons, and also alkyleneoxide adducts of $C_1$-$C_9$ alcohols such as Atlox®5000 from Uniqema or Hoe®-S3510 from Clariant;

b3) fatty acid and triglyceride alkoxylates such as the Serdox®NOG products from Condea, and alkoxylated vegetable oils such as soybean oil, rapeseed oil, corn kernel oil, sunflower oil, cottonseed oil, linseed oil, coconut oil, palm oil, safflower oil, walnut oil, peanut oil, olive oil or castor oil, especially rapeseed oil, for example the Emulsogen® products from Clariant;

b4) fatty acid amidealkoxylates such as the Comperlan® products from Henkel or the Amam® products from Rhodia;

b5) alkylene oxide adducts of alkynediols such as the Surfynol® products from Air Products, sugar derivatives such as amino and amido sugars from Clariant, Glukitole from Clariant, alkylpolyglycosides in the form of the APG® products from Henkel, or such as sorbitan esters in the form of the Span® or Tween® products from Uniqema, or cyclodextrin esters or ethers from Wacker;

b6) surface-active cellulose and algin, pectin and guar derivatives, such as the Tylose® products from Clariant, the Manutex® products from Kelco and guar derivatives from Cesalpina;

b7) polyol-based alkylene oxide adducts, such as Polyglykol® products from Clariant;

b8) interface-active polyglycerides and derivatives thereof from Clariant;

b9) sugar surfactants, for example alkoxylated sorbitan fatty acid esters, alkylpolyglycosides and the alkoxylated derivatives thereof;

b10) alkylene oxide adducts of fatty amines;

b11) surface-active compounds based on silicone or silane, such as the Tegopren® products from Goldschmidt and the SE® products from Wacker, and also the Bevaloid®, Rhodorsil® and Silcolapse® products from Rhodia (Dow Corning, Reliance, GE, Bayer);

b12) the interface-active sulfonamides, for example from Lanxess;

b13) neutral surfactant polyvinyl compounds such as modified polyvinylpyrollidone, such as the Luviskol® products from BASF and the Agrimer® products from ISP, or the derivatized polyvinyl acetates such as the Mowilith® products from Clariant, or the butyrates such as the Lutonal® products from BASF, the Vinnapas® and the Pioloform® products from Wacker, or modified polyvinyl alcohols such as the Mowiol® products from Clariant, and surface-active derivatives of montan, polyethylene and polypropylene waxes such as the BASF Luwax® products or the Licowet® products from Clariant;

b14) poly- or perhalogenated phosphonates and phosphinates such as Fluowet®-PL from Clariant;

b15) poly- or perhalogenated neutral surfactants, for example Emulsogen®-1557 from Clariant;

b16) (poly)alkoxylated, especially polyethoxylated, aromatic compounds such as (poly)alkoxylated phenols [=phenol (poly)alkylene glycol ethers], for example with 1 to 50 alkyleneoxy units in the (poly)alkyleneoxy moiety, where the alkylene moiety has preferably in each case 2 to 4 carbon atoms, preferably phenol reacted with 3 to 10 mol of alkylene oxide, (poly)alkylphenol alkoxylates [=polyalkylphenol (poly)alkylene glycol ethers], for example with 1 to 12 carbon atoms per alkyl radical and 1 to 150 alkyleneoxy units in the polyalkyleneoxy moiety, preferably tri-n-butylphenol or triisobutylphenol reacted with 1 to 50 mol of ethylene oxide, polyarylphenols or polyarylphenol alkoxylates [=polyarylphenol (poly)alkylene glycol ethers], for example tristyrylphenol polyalkylene glycol ether with 1 to 150 alkyleneoxy units in the polyalkyleneoxy moiety, preferably tristyrylphenol reacted with 1 to 50 mol of ethylene oxide and the condensation products thereof with formaldehyde—among these, preference is given to alkylphenol reacted with 4 to 10 mol of ethylene oxide, commercially available, for example, in the form of the Agrisol® products (Akcros), triisobutylphenol reacted with 4 to 50 mol of ethylene oxide, commercially available, for example, in the form of the Sapogenat® T products (Clariant), nonylphenol reacted with 4 to 50 mol of ethylene oxide, commercially available, for example, in the form of the Arkopal® products (Clariant), tristyrylphenol reacted with 4 to 150 mol of ethylene oxide, for example from the Soprophor® series such as Soprophor® FL or Soprophor® CY/8 (Rhodia);

the anionic substances of groups b17) to b23):

b17) anionic derivatives of the products described under b1) in the form of ether carboxylates, sulfonates, sulfates (=sulfuric monoesters) and phosphates (phosphoric mono- or diesters) of the substances described under b1) and the inorganic salts (e.g. $NH_4^+$, alkali metal and alkaline earth metal salts) and organic salts (e.g. based on amine or alkanolamine) thereof, such as Genapol®LRO, Sandopan® products, Hostaphat/Hordaphos® products from Clariant;

b18) anionic derivatives of the products described under b17) in the form of ether carboxylates, sulfonates, sulfates (=sulfuric monoesters) and phosphates (phosphoric mono- or diesters) of the substances described under b17), for example the acidic phosphoric ester of a $C_1$-$C_{16}$-alkylphenol ethoxylated with 2 to 10 mol of ethylene oxide, e.g. the acidic phosphoric ester of a nonylphenol reacted with 3 mol or with 9 mol of ethylene oxide, and the triethanolamine-neutralized phosphoric ester of the reaction product of 20 mol of ethylene oxide and 1 mol of tristyrylphenol;

b19) benzenesulfonates such as alkyl- or arylbenzenesulfonates, for example acidic (poly)alkyl- and (poly)arylbenzenesulfonates and those neutralized with suitable bases, for example having 1 to 12 carbon atoms per alkyl radical or having up to 3 styrene units in the polyaryl radical, preferably (linear) dodecylbenzenesulfonic acid and the oil-soluble salts thereof, for example the calcium salt or the isopropylammonium salt of dodecylbenzenesulfonic acid and acidic (linear) dodecylbenzenesulfonate, commercially, for example, in the form of the Marlon® products (Sasol);

b20) lignosulfonates such as sodium, calcium or ammonium lignosulfonates, such as Ufoxane® 3A, Borresperse AM® 320 or Borresperse® NA;

b21) condensation products of arylsulfonic acids such as phenolsulfonic acid or naphthalenesulfonic acid with formaldehyde and optionally urea, in particular the salts thereof and especially the alkali metal salts and calcium salts, for example the Tamol® and Wettol® brands from BASF SE, such as Wettol® D1;

b22) salts of aliphatic, cycloaliphatic and olefinic carboxylic acids and polycarboxylic acids, and also alpha-sulfo fatty acid esters as obtainable from Henkel;

b23) alkanesulfonates, paraffin- and olefinsulfonates such as Netzer IS®, Hoe®S1728, Hostapur®OS, Hostapur®SAS from Clariant;

and additionally cationic and zwitterionic products of groups b24) and b25):

b24) quaternary ammonium compounds having 8 to 22 carbon atoms ($C_8$-$C_{22}$), for example the Genamin®C, L, O, T products from Clariant;

b25) surface-active zwitterionic compounds such as taurides, betaines and sulfobetaines in the form of Tegotain® products from Evonik, Hostapon® and Arkopon® products from Clariant.

Among the alkyleneoxy units, ethyleneoxy, propyleneoxy and butyleneoxy units, especially ethyleneoxy units and mixtures of ethyleneoxy units and propyleneoxy units, are preferred. “Alkoxylated” means that the surface-active substance has a polyalkylene ether group, in particular a poly-$C_2$-$C_4$-alkylene ether group, especially a poly-$C_2$-$C_3$-alkylene ether group.

In a preferred embodiment, the active ingredient and the solubilizers used in accordance with the invention are present in the form of a formulation, i.e. in concentrated form. A formulation in the context of the invention comprises the inventive active ingredient(s) in a concentration of at least 10 g/l, preferably at least 50 g/l. Suitable formulations are, for example, water-soluble concentrates (SL, LS), redispersible concentrates (DC), emulsifiable concentrates (EC), emulsions (EW, EO, ES, ME), suspensions (SC, OD, FS), suspoemulsions (SE) or water-dispersible and water-soluble granules (WG, SG), water-dispersible and water-soluble powders (WP, SP, SS, WS) or gels (GF). The composition is preferably in the form of a water-soluble concentrate (SL), an emulsifiable concentrate (EC), a suspension concentrate (SC), water-dispersible and water-soluble granules (WG, SG) or a redispersible concentrate (DC), an oil-in-water emulsion or a microemulsion.

The formulations are usually diluted before use. Useful diluents are, as well as water, oil fractions of moderate to high boiling point, such as kerosene or diesel oil, and also coal tar oils and oils of vegetable or animal origin, aliphatic, cyclic and aromatic hydrocarbons, for example toluene, xylene, paraffin, tetrahydronaphthalene, alkylated naphthalenes or derivatives thereof, methanol, ethanol, propanol, butanol, cyclohexanol, cyclohexanone, isophorone, strongly polar solvents, for example dimethyl sulfoxide or N-methylpyrrolidone. Preference is given to using water or an aqueous system. It is also possible only to add the solubilizer at the stage of the dilute formulation. In this embodiment, the inventive use is in the form of a tankmix.

An aqueous system is understood to mean pure water or water comprising a buffer system or salts or further additives, for example water-miscible solvents or mixtures thereof. The pH of the aqueous system is generally in the range from 2 to 13, preferably from 3 to 12, more preferably from 4 to 10.

If appropriate, the dilute compositions may comprise 0.1-5% by weight of buffer based on the total amount of the formulation produced for pH regulation, the amount and type of the buffer used being guided by the chemical properties of the active ingredient or of the active ingredients. Examples of buffers are alkali metal salts of weak inorganic or organic acids, for example phosphoric acid, boric acid, acetic acid, propionic acid, citric acid, fumaric acid, tartaric acid, oxalic acid and succinic acid.

The diluted composition, preferably an aqueous application form, is typically applied by spraying or nebulizing. It is possible to add oils of various types, wetting agents, adjuvants, further active ingredients such as herbicides, bactericides or fungicides immediately before the tankmix application. These agents can be added to the inventive compositions in a weight ratio of 1:100 to 100:1, preferably 1:10 to 10:1. The termiticide concentration in the tankmix can vary within relatively wide ranges.

In a preferred embodiment, the active insecticidal ingredient and the polymeric solubilizer are used as an SL formulation. By definition, SL formulations are water-soluble concentrates which comprise the active ingredient(s), if appropriate with further formulation aids, dissolved in suitable solvent, and are present as a clear or opalescent liquid. They are characterized in that, even after dilution in the spray liquor, they form a true solution of the active ingredient in water (FAO&WHO Specification for Pesticides (March 2006)).

Preference is also given to use as a WG, SC, EW, ME or DC formulation.

In a further preferred embodiment of the invention, the combination of active ingredient, polymeric solubilizer and any adjuvant is used as a tankmix, i.e. the polymeric solubilizer and/or any adjuvant are only added at the stage of the aqueous application form (spray liquor).

The formulations or tankmixes used in accordance with the invention, and aqueous application forms obtained therefrom, exhibit increased soil mobility of the sparingly soluble termiticides used. They are thus suitable for control of pests living in the soil, for example in the protection of materials and buildings or plants. More preferably, the inventive formulations are suitable for controlling termites, ants and nematodes, especially for controlling termites.

The invention therefore also provides a method for controlling soil-dwelling invertebrate pests, wherein a) at least one sparingly soluble active insecticidal ingredient, especially fipronil, and
b) at least one polymeric solubilizer which has the property that the active termiticidal ingredient in a 1% by weight aqueous solution of the polymeric solubilizer at 25° C. and 1.01325 bar has a solubility at least forty times higher than under the same conditions in pure water, and is selected from the group of the above-specified solubilizers A (especially A1, A2 and/or A3), B1, B3, B5, G and H in a weight ratio (a:b)≤1 in an aqueous application form are applied to or into a soil used by the pests.

In a preferred embodiment, the pests are ants.

In a further preferred embodiment, a sugarbeet crop is present on the soil.

In a further particularly preferred embodiment, the pests are ants and a sugarbeet crop is present on the soil.

In a further preferred embodiment, the pests are nematodes.

The invention further provides a method for controlling termites, wherein a) at least one sparingly soluble active insecticidal ingredient, especially fipronil, and
b) at least one polymeric solubilizer which has the property that the active termiticidal ingredient in a 1% by weight aqueous solution of the polymeric solubilizer at 25° C. and 1.01325 bar has a solubility at least forty times higher than under the same conditions in pure water, and is selected from the group of the above-specified solubilizers A (especially A1, A2, A3), B1, B3, B4, C, D, E, F, G and H, preferably A (especially A1, A2, A3), B1, B3 and B5, more preferably A (especially A1) and B1, in a weight ratio (a:b)≤1 in an aqueous application form are applied to or into a soil used by the termites.

In a preferred embodiment, the soil is the soil below a building or within a radius of 10 m around a building.

In the protection of buildings from termites, the legal requirements in some countries dictate the application of the termiticide in trenches of a certain width and depth. Trenches of 6×6 inches (15.24×15.24 cm) in size are customary, as prescribed, for example, in the USA.

The inventive increase in the soil mobility of the active termiticidal ingredients makes it possible to apply the termiticide in trenches with smaller dimensions or directly to the soil. If appropriate, a more highly concentrated application solution may also be used in order to reduce the volume of water used. In a further particularly preferred embodiment of the method according to the invention, it is performed to protect buildings from termites, and the termiticide, especially fipronil, is applied to the soil used by the termites in a trench with a depth of <3 inches (7.62 cm), preferably in a trench with a depth of 3 to 1 inch (7.62-2.54 cm). Preference is further given to an application form in which the concentration of the active termiticidal ingredient(s) in the aqueous application form is at least 1000 ppm, preferably at least 1250 ppm.

Preference is given in the above methods to the use of a sparingly soluble insecticide from the group of fipronil, pyrethroids, 4-chloro-2-(2-chloro-2-methylpropyl)-5-[(6-iodo-3-pyridinyl)methoxy]-3(2H)-pyridazinones (CAS-RN: 120955-77-3), chlorantraniliprole, chlorfenapyr, chlorpyrifos, cyantraniliprole, fenoxycarb, flufenoxuron, hydramethylnon, imidacloprid, indoxacarb, metaflumizone, pyriproxifen and tebufenozide.

Preferred termiticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl) methoxy]-3(2H)-pyridazinones (CAS-RN: 120955-77-3), chlorantraniliprole, chlorfenapyr, chlorpyrifos, cyantraniliprole, cyfluthrin, cyhalothrin, cypermethrin, deltamethrin, etofenprox, fenoxycarb, flufenoxuron, hydramethylnon, imidacloprid, indoxacarb, metaflumizone, permethrin, pyriproxifen, tebufenozide and tralomethrin. Particular preference is given to fipronil, alpha-cypermethrin, bifenthrin, chlorantraniliprole, chlorfenapyr, cyfluthrin, cypermethrin, cyantraniliprole, deltamethrin, etofenprox, hydramethylnon, indoxacarb, metaflumizone and permethrin. Very particular preference is given to fipronil, alpha-cypermethrin, chlorantraniliprole, chlorfenapyr, cyantraniliprole, deltamethrin, hydramethylnon, indoxacarb and metaflumizone. Fipronil is especially preferred.

Preferred solubilizer(s) are the polymers of group A (especially A1, A2 and/or A3), B1 and B3 and/or B5, more preferably A (especially A1) and/or B1.

Preference is also given to combinations of the preferred, particularly preferred, very particularly preferred and especially preferred active ingredients with appropriate solubilizer(s).

Preference is given to using active ingredient, polymeric solubilizer and if appropriate adjuvant as a formulation. Likewise preferably, polymeric solubilizer and if appropriate adjuvant is added as a tankmix to the aqueous application form.

Particular preference is given to combinations of fipronil (a) with at least one solubilizer (b) of groups A (especially A1, A2 and/or A3) and/or B1.

Inventive methods are suitable preferentially for controlling termites (Isoptera), preferably soil termites, especially of the *Reticulitermes* genus, for example the species *R. flavipes, R. virginicus, R. hageni, R. hesperus, R. okanaganensis, R. malletei, R. fibialis; R. grassei, R. banyulensis, R. balkanensis and R. urbis*; the *Coptotermes* genus, for example the species *C. testaceus, C. gestroi* and *C. formosanus*; the *Heterotermes* genus, for example the species *H. aureus, H. tenuis, H. convexinotatus* and *H. cardini*; and dry wood termites, especially of the *Incisitermes* genus, especially the species *I. snyderi* and *I. minor*; and the *Cryptotermes* genus, especially the species *C. brevis* and *C. cavifrons*.

Ants which can be controlled in accordance with the invention are, for example, from the *Atta* genus, such as *Atta cephalotes, Atta capigura, Atta cephalotes, Atta laevigata, Atta robusta, Atta sexdens, Atta texana*; the *Crematogaster* genus; *Lasius* genus; the *Monorium* genus, such as *Monorium pharaonis*, the *Solenopsis* genus such as *Solenopsis geminata, Solenopsis invicta, Solenopsis richteri, Solenopsis xyloni*; the *Pogonomyrmex* genus, such as *Pogonomyrmex barbatus, Pogonomyrmex californicus*; the *Pheidole* genus, such as *Pheidole megacephala*, the *Dasymutilla* genus, such as *Dasymutilla occidentalis*; the *Camponotus* genus, such as *Camponotus floridanus*; and the *Linepithema* genus, such as *Linepithema humile.*

Plant nematodes which can be controlled in accordance with the invention are, for example, *Angunina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radapholus similis, Rotylenchus* spp., *Trichodorus* spp., *Tylenchorhynchus* spp., *Tylenchulus* spp., *Tylenchulus semipenetrans* and *Xiphinema* spp.

Some of the formulations used in accordance with the invention are known and some of them are novel.

The invention also provides the formulation (F1) comprising a) one or more active ingredients from the group of fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)-pyridazinone (CAS-RN: 120955-77-3), chlorantraniliprole, chlorfenapyr, chlorpyrifos, cyantraniliprole, cyfluthrin, cyhalothrin, cypermethrin, deltamethrin, etofenprox, fenoxycarb, flufenoxuron, hydramethylnon, imidacloprid, indoxacarb, metaflumizone, permethrin, pyriproxifen, tebufenozide and tralomethrin, and
b) at least one polymeric solubilizer which has the property that the active termiticidal ingredient in a 1% by weight aqueous solution of the polymeric solubilizer at 25° C. and 1.01325 bar has a solubility at least forty times higher than under the same conditions in pure water from the above-described groups A1, B1, B3, B5, G and H in a weight ratio (a:b) of ≤1.

Preferred, particularly preferred, very particularly preferred and especially preferred active ingredients (a) are those specified in each case in the inventive methods.

Preferred solubilizer(s) (b) are polymers from the group of components A1, B1, B3 and/or B5, more preferably A1.

More preferably, the (weight) ratio of active ingredient(s) and polymeric solubilizer(s) is from 1:1 to 1:20, more preferably from 1:1 to 1:10, most preferably from 1:1 to 1:8.

In one embodiment of the invention, the formulations comprise, as well as active ingredient(s) and solubilizer(s), one or more above-described adjuvants from groups Z1-Z13. In a further preferred embodiment, the formulation (F1) does not comprise an adjuvant from groups Z1-Z13, preferably Z1-Z12.

The formulation (F1) is preferably an SL formulation. Equally preferably, the formulation (F1) is a WG, SC, ME, EW or a DC formulation.

The invention also provides an SL, SC, WG or DC formulation, preferably SL or DC formulation, especially SL formulation (F2), comprising a) fipronil and
b) at least one polymeric solubilizer which has the property that the active termiticidal ingredient in a 1% by weight aqueous solution of the polymeric solubilizer at 25° C. and 1.01325 bar has a solubility at least forty times higher than under the same conditions in pure water, from the above-described groups A to H, in a weight ratio (a:b) of ≤1.

Preferred solubilizers (b) are compounds of groups A (A1, A2, A3), B1, B2, B3 and/or B5, more preferably A (A1, A2, A3) and/or B1, especially A (preferably A1).

The (weight) ratio of active ingredient(s) and solubilizer(s) is preferably from 1:1 to 1:20, more preferably from 1:1 to 1:10, most preferably from 1:1 to 1:8.

In one embodiment of the invention, the formulation (F2) comprises, as well as active ingredient(s) and solubilizer(s), one or more above-described adjuvants from the groups Z1-Z13. In a further embodiment of the invention, the SL formulation (F2) does not comprise any adjuvants from groups Z1-Z13, preferably Z1-Z12.

The invention further provides a formulation (F3) comprising a) one or more active ingredients from the group of fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)-pyridazinone (CAS-RN: 120955-77-3), chlorantraniliprole, chlorfenapyr, chlorpyrifos, cyantraniliprole, cyfluthrin, cyhalothrin, cypermethrin, deltamethrin, etofenprox, fenoxycarb, flufenoxuron, hydramethylnon, imidacloprid, indoxacarb, metaflumizone, permethrin, pyriproxifen, tebufenozide and tralomethrin, b) at least one polymeric solubilizer which has the property that the active termiticidal ingredient in a 1% by weight aqueous solution of the polymeric solubilizer at 25° C. and 1.01325 bar has a solubility at least forty times higher than under the same conditions in pure water, from the above-described groups A-H in a weight ratio (a:b) of ≤1 and c) one or more of the above-described adjuvants from groups Z1-Z13, preferably Z1-Z12.

Preferred, particularly preferred, very particularly preferred and especially preferred active ingredients (a) are those specified in each case in the inventive methods.

Preferred solubulizer(s) (b) are polymers from group A (especially A1, A2, A3), B1, B2, B3 and/or B5, more preferably A (especially A1, A2, A3) and/or B1, especially A (especially A1).

The (weight) ratio of active ingredient(s) and polymeric solubilizer(s) is more preferably from 1:1 to 1:20, more preferably from 1:1 to 1:10, most preferably from 1:1 to 1:8.

Preference is given to a WG, SC, DC, SC, ME or EW formulation in which active ingredient(s) and solubilizer(s) are present in concentrated form, which is diluted with water for application, preference being given to a dilution factor of 1:3000 to 1:10, especially from 1:1000 to 1:50.

In a preferred embodiment of the invention, the formulation F3 comprises one or more of the above-described adjuvants from groups Z1, Z4 and/or Z13, especially Z1 and/or Z4.

The inventive formulations F1, F2, F3 are suitable preferentially for use in the process according to the invention.

Reference is hereby made explicitly to the following documents—especially with regards to the description of the solubilizers A-H—they form part of this description by reference: WO 2009/021986 (A), European Patent Application EP 09159881.3 (A1), WO 2007/125028 (A2), WO 2006/087227 (A3), WO 99/27916 (B1), WO 2007/017452 (B1), WO 2008/064990 (B1), WO 2008/058848 (B2), WO 2007/065845 (B3), WO 2008/064987 (B4) (E), WO 2006/018135 (B5), WO 2008/065050 (C), WO 2008/064986 (D), WO 2008/040786 (F), EP-A 0 947 243 (G) and WO 03/055944 (H).

The invention is illustrated in detail by the examples, without thereby limiting it.

EXAMPLES

Abbreviations

AIBN: azobis(isobutyronitrile)

AMPS: 2-acrylamido-2-methylpropanesulfonic acid

DBTL: dibutyltin dilaurate

IP: isopropanol

IPDI: isophorone diisocyanate

IT: internal temperature

LA: lauryl acrylate

MA: maleic anhydride

NaA: sodium acrylate

PEGMEMA 475: polyethylene glycol monomethyl ether methacrylate (M=475 g/mol)

S: styrene

T: feed time

TBPPiv: t-butyl perpivalate

TMP×15.7 PO: reaction product of trimethylolpropane with a 15.7 molar excess of propylene oxide VP: vinylpyrrolidone Materials Used a) Active termiticidal ingredients Fipronil was used as a commercial SC formulation, Termidor® (comprising 96 g/l of Fipronil, BASF SE), or as a technical grade active ingredient with a purity of approx. 90%.

b) Solubilizers

Solubilizers of group B1:

| | Composition [% by weight] | | | |
|---|---|---|---|---|
| Designation | VP | LA | NaA | AMPS |
| S1 | 90 | 10 | — | — |
| S2 | 80 | 20 | — | — |
| S3 | 70 | 30 | — | — |
| S4 | 78 | 20 | 2 | — |
| S5 | 70 | 20 | 10 | — |
| S6 | 76 | 20 | 2 | 2 |

Solubilizers of group D:

S7: MA/S (50:50 mol %), 50% of the MA units having been esterified with a $C_{13}$ fatty alcohol alkoxylate.

Solubilizers of group A (A1):

Solubilizer S8 (hyperbranched polycarbonate based on diethyl carbonate and the reaction product of trimethylolpropane with a 15.7 molar excess of propylene oxide functionalized with PEG chains (degree of functionalization 100%))

Solubilizer S9 (hyperbranched polycarbonate based on diethyl carbonate and the reaction product of trimethylolpropane with a 15.7 molar excess of propylene oxide functionalized with a comb-type PVP-co-Plaurylacrylate-co-PEGMEMA copolymer (degree of functionalization 50%))

Solubilizer S10 (hyperbranched polycarbonate core based on diethyl carbonate and the reaction product of trimethylolpropane with a 15.7 molar excess of propylene oxide functionalized with PEG-b-polycaprolactone block copolymer (degree of functionalization 100%)

c) Adjuvants

Soprophore 4D384:

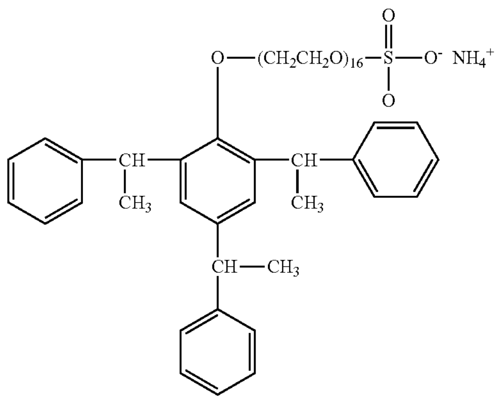

Break Thru® S 240 (Evonik): nonionic surfactant based on modified polysiloxane polyethers Synthesis Examples for Solubilizers Example 1

Solubilizer S1 (N-vinylpyrrolidone/lauryl acrylate copolymer [90/10% by weight])

The initial charge (350 g of isopropanol, 10 g of N-vinylpyrrolidone) was sparged with nitrogen and heated to an internal reactor temperature of 80° C. Subsequently, the addition of feeds 1-3 was commenced. Feed 1 (400 g of isopropanol, 40 g of lauryl acrylate) was added within 5.5 h, feed 2 (300 g of isopropanol, 350 g of N-vinylpyrrolidone) within 6 h, and feed 3 (19 g of ϵ-butyl perpivalate 75%, 100 g of isopropanol) within 6.5 h. The mixture was polymerized further for another 2 h. Subsequently, the isopropanol was distilled off and the reaction mixture was subjected to a steam distillation. After distillation, the polymer solution was diluted with 200 g of water.

This afforded a polymer with a K value of 14 and a molar mass $M_n$ of 4400 g/mol and $M_w$ of 7600 g/mol.

The solubilizers S2 and S3 were prepared correspondingly:

S2: 80 g of lauryl acrylate and feed 2 with 310 g of N-vinylpyrrolidone $M_n$=2500 g/mol and $M_w$=5000 g/mol, K value=12

S3: 120 g of lauryl acrylate and feed 2 with 270 g of N-vinylpyrrolidone $M_n$=1300 g/mol and $M_w$=2900 g/mol, K value=7

Example 2

Solubilizer S4 (VP/LA/sodium acrylate copolymer [78/20/2])

The initial charge (19.13 g of feed 1) was sparged with nitrogen and heated to an internal reactor temperature of 80° C. Subsequently, the addition of feeds 1-4 was commenced. Feed 1 (400 g of isopropanol, 80 g of lauryl acrylate) was added within 5.5 h, feed 2 (300 g of isopropanol, 312 g of VP) and feed 3 (50 g of $H_2O$, 21 g of 37.5% by weight solution of sodium acrylate) within 6 h, and feed 4 (100 g of isopropanol, 19 g of t-butyl perpivalate) within 6.5 h. The mixture was then polymerized further for 2 h. The isopropanol was distilled off and the reaction mixture was subjected to a steam distillation. After distillation, the polymer solution was diluted with 200 g of water.

This afforded a polymer with a K value of 12 and a molar mass Mn=2300 g/mol.

Solubilizer S5 was prepared correspondingly:

S5 (VP/LA/NaA [70/20/10]) Copolymer

Analogously to example 2, with 280 g of VP and 105 g of a 37.5% by weight sodium acrylate solution.

This afforded a polymer with a K value of 12 and a molar mass Mn=2100 g/mol.

Example 3

Solubilizer S6 (VP/LA/AMPS-Na/NaA 76:20:2:2)

The initial charge (250 g of isopropanol, 25 g of N-vinylpyrrolidone, 25 g of lauryl acrylate) was sparged with nitrogen and heated to an internal reactor temperature of 75° C. Then feed 1 (350 g of isopropanol, 165 g of N-vinylpyrrolidone, 25 g of lauryl acrylate), feed 2 (222 g of water, 28 g of AMPS sodium salt, pH7) and feed 3 (27 g of water, 13 g of sodium acrylate) were added within 3 h. Feed 4 (47.5 g of water, 2.5 g of 2,2'-azobis(2-methylpropionamidine) dihydrochloride [WAKO® V 50, Wako Chemicals]) was added within 4.5 h. After continued polymerization for 1 h, feed 5 (10 g of water, 0.65 g of 2,2'-azobis(2-methylpropionamidine) dihydrochloride [WAKO® V 50]) was added, and polymerization was continued for 2 h. The isopropanol was distilled off and the reaction mixture was subjected to a steam distillation.

This afforded a polymer with a K value of 22 and a molar mass $M_n$ of 9700 g/mol and $M_W$ of 31 300 g/mol.

Example 4

Solubilizer S7 (Maleic Anhydride/Styrene (50/50) Copolymer Partly Esterified with $C_{13}$ Fatty Alcohol Alkoxylate)

The initial charge (100 g of MA/S copolymer [SMA® 100 F, Sartomer], 575 g of $C_{13}$ fatty alcohol alkoxylate) was sparged with nitrogen and heated to an internal reactor temperature of 150° C. The reaction mixture was then stirred at this temperature for 4 h.

This afforded a polymer with a K value of 12 and a molar mass Mn=2300 g/mol.

Example 5

Solubilizer S8 (Hyperbranched Polycarbonate Based on Diethyl Carbonate and the Reaction Product of Trimethylolpropane with a 15.7 Molar Excess of Propylene Oxide, Functionalized with Peg Chains (Degree of Functionalization 100%)).

5.1 Hyperbranched polycarbonate core with terminal hydroxyl groups 2298 g of TMP×15.7 PO, 284 g of diethyl carbonate and 2 g of DBTL catalyst were initially charged and heated to boiling. The boiling reaction mixture was stirred (approx. 14 h) until the boiling temperature of the reaction mixture had fallen as a result of the evaporative cooling of the ethanol released to a constant temperature of approx. 143° C. The reflux condenser was then replaced by a distillation apparatus and the ethanol formed in the reaction was distilled off, in the course of which the temperature of the reaction mixture was increased to 230° C. The ethanol was collected in a cooled round bottomed flask and weighed, and the conversion was thus determined as a percentage relative to the theoretically possible full conversion. After the attainment of a conversion of 89%, dry nitrogen was passed through the reaction mixture at a temperature of 160° C. for 1 hour, in order to remove residual amounts of monomers still present. Thereafter, the mixture was cooled to room temperature.

The polymer formed (Mn=2400 g/mol; Mw=4600 g/mol; OH number: 87 mg KOH/g of polymer) was obtained in the form of a yellow, highly viscous liquid which was not water-soluble.

5.2 Hyperbranched polycarbonate core, functionalized with PEG chains (degree of functionalization 100%)

5.2.1 123.5 g of polyethylene glycol monomethyl ether (Mn=500 g/mol) were initially charged and freed of water residues at 80° C. under reduced pressure. After cooling to room temperature, the mixture was placed under nitrogen and the polymer was dissolved in 123.5 g of butyl acetate. 50.0 g of isophorone diisocyanate were then added and the mixture was heated to 50° C. Addition of 19 mg of zinc neodecanoate dissolved in 1 ml of butyl acetate started the reaction which was conducted at 50° C. over the course of 3.5 h down to an NCO content of 2.87%. Subsequently, the reaction was ended by cooling to −20° C. The reaction product was used directly in stage 5.2.2 without further workup.

5.2.2 30.1 g of the hydrophobic hyperbranched polycarbonate core from stage 5.1 was initially charged and admixed under nitrogen with 71.0 g of the reaction mixture 5.2.1. The mixture was then heated to 80° C. and the reaction was started by adding 7 mg of DBTL dissolved in 1 ml of butyl acetate. After the complete conversion of all NCO groups (NCO content 0%), the mixture was cooled and the solvent was removed under reduced pressure. Finally, the solubilizer S8 (Mn=5070 g/mol) was obtained in the form of a yellow, highly viscous liquid which was completely water-soluble.

Example 6

Solubilizer S9 (Hyperbranched Polycarbonate Based on Diethyl Carbonate and the Reaction Product of Trimethylolpropane with a 15.7 Molar Excess of Propylene Oxide, Functionalized with a Comb-Type PVP-co-PLauryl Acrylate-co-PEGMEMA Copolymer (Degree of Functionalization 50%)).

6.1 Hyperbranched polycarbonate core with terminal hydroxyl groups 1149 g of the trifunctional alcohol TMP× 15.7 PO, 144 g of diethyl carbonate and 1 g of DBTL catalyst were reacted as in synthesis example 5.1. The polymer formed (Mn=4200 g/mol; Mw=14 500 g/mol; OH number: 85 mg KOH/g of polymer) was obtained in the form of a yellow, highly viscous liquid which was not water-soluble.

6.2 Hyperbranched polycarbonate core functionalized with a comb-type PVP-co-PLauryl acrylate-co-PEGMEMA copolymer (degree of functionalization 50%)

6.2.1 100.0 g of THF were initially charged under nitrogen and then heated under reflux. Within 3 h, a mixture 1 of 155.9 g of lauryl acrylate, 144.2 g of N-vinylpyrrolidone and 163.3 g of PEGMEMA 475, dissolved in 200.0 g of THF, and simultaneously, within 4 h, a mixture 2 of 8.8 g of AIBN and 27.8 g of mercaptoethanol, dissolved in 200.0 g of THF, were added slowly to the mixture with the aid of two metering pumps. After addition of mixture 2 had ended, the reaction mixture was heated under reflux for a further 18 h. Subsequent monitoring of the residual monomers by means of GC showed a content of lauryl acrylate of <1%, and so the mixture was cooled and the product (Mn=1000 g/mol) was directly used further in stage 2.

6.2.2 278.4 g of reaction mixture 6.2.1 were initially charged and freed of the THF solvent under reduced pressure. After cooling to room temperature, the mixture was placed under nitrogen and the residue was dissolved in 140.0 g of butyl acetate. Then 20.0 g of isophorone diisocyanate were added and the mixture was heated to 50° C. Addition of 21 mg of zinc neodecanoate dissolved in 1 ml of butyl acetate started the reaction which was conducted at 60° C. over the course of 6 h and at room temperature for a total of 16 h down to an NCO content of 1.16%. The reaction was ended by cooling to −20° C. The reaction product was used directly in stage 3 without further workup.

6.2.3 6.0 g of the hydrophobic hyperbranched polycarbonate core 6.1 were initially charged and dissolved in 6.0 g of butyl acetate under nitrogen. The mixture was then admixed with 19.2 g of reaction mixture 6.2.2 and heated to 80° C., and the reaction was started by adding 13 mg of DBTL dissolved in 1 ml of butyl acetate. On completion of conversion of all NCO groups (NCO content 0%), the mixture was cooled and the solvent was removed under reduced pressure. Finally, the solubilizer S9 (Mn=8110 g/mol) was obtained in the form of a yellow, highly viscous liquid which was completely water-soluble.

Example 7

Solubilizer S10 (Hyperbranched Polycarbonate Core Based on Diethyl Carbonate and the Reaction Product of Trimethylolpropane with a 15.7 Molar Excess of Propylene Oxide, Functionalized with PEG-b-Polycaprolactone Block Copolymer (Degree of Functionalization 100%)).

7.1 Hyperbranched polycarbonate core with terminal hydroxyl groups 1149 g of the trifunctional alcohol TMP× 15.7 PO, 144 g of diethyl carbonate and 1 g of DBTL catalyst were converted as in synthesis example 2. The polymer formed (Mn=4200 g/mol; Mw=14 500 g/mol; OH number: 85 mg KOH/g of polymer) was obtained in the form of a yellow, highly viscous liquid which was not water-soluble.

7.2 Hyperbranched polycarbonate core functionalized with PEG-b-polycaprolactone block copolymer (degree of functionalization 100%)

7.2.1 150.0 g of polyethylene glycol monomethyl ether (Mn=500 g/mol) were initially charged and freed of water residues at 90° C. under reduced pressure. After cooling to room temperature, the mixture was placed under nitrogen and the polymer was admixed with 205.0 g of ϵ-caprolactone. The mixture was heated to 90° C. and the ring-opening polymerization of the caprolactone was started by adding 355 mg of butyltin tris(2-ethylhexanoate). The mixture was heated at 90° C. for a further 18 h and, after the reaction had ended, cooled to room temperature. The OH-terminated block copolymer thus obtained (Mn=1180 g/mol) was used directly in stage 2 without further purification.

7.2.2 200.0 g of block copolymer 7.2.1 were initially charged, placed under nitrogen and admixed with 34.1 g of isophorone diisocyanate. The mixture was heated to 50° C. Addition of 30 mg of zinc neodecanoate dissolved in 1 ml of butyl acetate started the reaction which was conducted at 50° C. over the course of 4 h down to an NCO content of 2.23%. Subsequently, the reaction was ended by cooling to −20° C. The reaction product was used directly in stage 7.2.3 without further workup.

7.2.3 7.0 g of the hydrophobic hyperbranched polycarbonate core 7.1 were initially charged and dissolved in 10.0 g of butyl acetate under nitrogen. The mixture was then admixed with 20.0 g of reaction mixture 7.2.2 and heated to 80° C., and the reaction was started by adding 27 mg of DBTL dissolved in 1 ml of butyl acetate. On completion of conversion of all NCO groups (NCO content 0%), the mixture was cooled and the solvent was removed under reduced pressure. Finally, the solubilizer S10 (Mn=13 190 g/mol) was obtained in the form of a yellow, highly viscous liquid which was completely water-soluble.

Application Examples

Example 8

Solubilization of Fipronil (Technical Grade Active Ingredient, Purity 89.8%) with Commercial Adjuvants and Solubilizers Used in Accordance with the Invention

| Adjuvant | Adjuvant conc. in % | Fipronil solubility in ppm |
|---|---|---|
| None | 0 | 2.2 |
| Soprophor 4D384 | 1.0 | 5.9 |
| GK 2303/012 | 1.0 | 11 |
| Break Thru S 240 | 1.0 | 10 |
| Triton X-100 | 1.0 | 13 |
| Silwet L77 | 1.0 | 52.3 |
| Wettol LF 700 | 1.0 | 10 |
| Lutensol ON 70 | 1.0 | 63.2 |
| Rhodapex CD-128 | 1.0 | 11.3 |
| Plurafac LF 901 | 1.0 | 78.3 |
| **Solubilizer** | **Solubilizer conc. in %** | **Fipronil solubility in ppm** |
| S5 VP:lauryl acrylate:sodium acrylate 70:20:10 (% weight) | 1.0 | 156.8 |
| S4 VP:lauryl acrylate:sodium acrylate 78:20:2 (% weight) | 1.0 | 189.2 |
| S1 VP:lauryl acrylate 90:10 (% weight) | 1.0 | 119.6 |
| S2 VP:lauryl acrylate 80:20 (% weight) | 1.0 | 197.7 |
| S3 VP:lauryl acrylate 70:30 (% weight) | 1.0 | 189.4 |
| S6 MSA/styrene/Plurafac LF 401 | 1.0 | 143.2 |
| S7 VP/LA/AMPS-Na/Na acrylate 76:20:2:2 (% weight) | 1.0 | 115.8 |
| S9 | 1.0 | 179 |

The fipronil concentration was determined by means of UV spectroscopy at 278 nm; to this end, the absorption of the polymer (1% by weight in water) was first determined alone. Subsequently, an excess of fipronil was added and the mixture was stirred at room temperature overnight. The centrifuged solution was analyzed once again at 278 nm in the UV instrument. After subtracting the appropriate solubilizer spectrum and comparing by means of a fipronil calibration curve produced beforehand, it was possible to determine the concentration of dissolved fipronil.

Test Setup

A glass column composed of six segments with a length of 27.5 cm, a diameter of 5 cm and a surface (a cross section) of 19.6 $cm^2$ was, with the aid of a vibrator, filled with soil (LUFA 2.3 (sandy Loam) [USDA], pH 7.2, air-dried, TOC 1%, density 1.24 $g/cm^3$, max WHC 28.9 g/100 g).

Inventive and comparative formulations were applied to this column (60 ml, comprising 37.5 mg of fipronil (625 ppm) with or without appropriate amounts of solubilizer). After application, a further 40 ml of water were applied.

HPLC-MSD was used to measure how much in % of the amount of fipronil originally applied (625 ppm, 37.5 mg) was present in the segments of the column (0-2.5 cm, 2.5-7.5 cm, 7.5-12.5 cm, 12.5-17.5 cm and 17.5-22.5 cm).

The soil mobility relative to the Termidor SC commercial product was calculated by the following method:

Soil mobility=(fipronil content [%] in segment 1)×2.5+(fipronil content [%] in segment 2)×7.5+(fipronil content [%] in segment 3)×12.5+ . . . +(fipronil content [%] in segment 6)×27.5/(fipronil content [%] in segment 1 Termidor *SC*)×2.5+(fipronil content [%] in segment 2 Termidor *SC*)×7.5+(fipronil content [%] in segment 3 Termidor *SC*)×12.5+ . . . +(fipronil content [%] in segment 6 Termidor *SC*)×27.5)

Tankmix Formulations (Table 1)

An appropriate amount of fipronil (as Termidor® SC) was added to an aqueous solution of polymer with or without adjuvants, such that the concentration of fipronil was 625 ppm. 60 ml of each solution obtained were applied to the column described.

The soil mobility was calculated as described above—the reference used was again Termidor SC:

TABLE 1

Tankmix tests

| Ex No. | Polymer concentration | Fipronil (625 ppm) and solubilizer | Adjuvant | Conc. | Soil depth (cm) 0-2.5 | Soil depth (cm) 2.5-7.5 | Soil depth (cm) 7.5-12.5 | Soil depth (cm) 12.5-17.5 | Soil depth (cm) 17.5-22.5 | Soil depth (cm) 22.5-27.5 | Mobility relative to Termidor SC |
|---|---|---|---|---|---|---|---|---|---|---|---|
| V1 | — | — | — | | 83 | 17 | 0 | 0 | 0 | 0 | 100 |
| V2 | 300 ppm | S1 | — | | 94 | 5 | 1 | 0 | 0 | 0 | 84 |
| 9 | 625 ppm | S3 | — | | 65 | 30 | 5 | 0 | 0 | 0 | 133 |
| 10 | 625 ppm | S8 | — | | 72 | 25 | 3 | 0 | 0 | 0 | 120 |
| 11 | 625 ppm | S2 | — | | 66 | 27 | 6 | 1 | 0 | 0 | 136 |

TABLE 1-continued

| Tankmix tests | | | | | | | | | | | | |
|---|---|---|---|---|---|---|---|---|---|---|---|---|
| Ex No. | Polymer concentration | Fipronil (625 ppm) and solubilizer | Adjuvant | Conc. | Soil depth (cm) 0-2.5 | Soil depth (cm) 2.5-7.5 | Soil depth (cm) 7.5-12.5 | Soil depth (cm) 12.5-17.5 | Soil depth (cm) 17.5-22.5 | Soil depth (cm) 22.5-27.5 | Mobility relative to Termidor SC |
| 12 | 0.19% | S8 | Soprophor 4D384 | 0.062% | 37 | 41 | 18 | 4 | 0 | 0 | 125 * |
| 13 | 0.50% | S2 | — | | 53 | 40 | 7 | 0 | 0 | 0 | 154 |
| 14 | 1.00% | S2 | — | | 38 | 53 | 9 | 0 | 0 | 0 | 179 |
| 15 | 3.00% | S2 | — | | 24 | 47 | 25 | 2 | 1 | 1 | 240 |
| 16 | 1.00% | S2 | Soprophor 4D384 | 0.50% | 33 | 46 | 17 | 3 | 1 | 0.4 | 215 |
| 17 | 1.00% | S2 | Soprophor 4D384 | 1% | 49 | 33 | 11 | 7 | 1 | 0.4 | 197 |
| 18 | 1.00% | S2 | Break Thru S240 | 2% | 30 | 44 | 20 | 4 | 1 | 0.9 | 229 |
| 19 | 1.00% | S2 | Soprophor 4D384 and Break Thru S240 | 1.0% + 1.0% | 63 | 25 | 7 | 4 | 1 | 0 | 156 |
| V3 | — | — | Soprophor 4D384 | 625 ppm | 80 | 20 | 0 | 0 | 0 | 0 | 104 |
| V4 | — | — | Soprophor 4D384 | 0.2% | 77 | 23 | 0 | 0 | 0 | 0 | 108 |
| V5 | — | — | Soprophor 4D384 | 0.5% | 73 | 24 | 3 | 0 | 0 | 0 | 119 |
| V6 | — | — | Soprophor 4D384 and Break Thru S240 | 1.5 + 1.5% | 33 | 45 | 19 | 3 | 0 | 0 | 210 |
| V7 | — | — | Break Thru S240 | 3 | 43 | 44 | 11 | 2 | 0 | 0 | 181 |
| 20 | 3 | S2 | Soprophor 4D384 | 0.5 | 39 | 42 | 16 | 3 | 0 | 0 | 197 |
| 21 | 3 | S2 | Soprophor 4D384 | 2 | 17 | 42 | 23 | 16 | 2 | 0 | 287 |
| 22 | 3 | S2 | Soprophor 4D384 | 3 | 17 | 33 | 27 | 19 | 3 | 1 | 313 |
| 23 | 0.5 | S2 | Soprophor 4D384 | 3 | 25 | 51 | 15 | 7 | 2 | 0 | 237 |
| 24 | 0.5 | S2 | Break Thru S240 | 3 | 36 | 53 | 10 | 1 | 0 | 0 | 187 |

* based on a different standard

TABLE 1a

| Tankmix tests | | | | | | | | | | | |
|---|---|---|---|---|---|---|---|---|---|---|---|
| Ex No. | Polymer concentration | Fipronil (1250 ppm) solubilizer | Adjuvant | Conc. | Soil depth (cm) 0-2.5 | Soil depth (cm) 2.5-7.5 | Soil depth (cm) 7.5-12.5 | Soil depth (cm) 12.5-17.5 | Soil depth (cm) 17.5-22.5 | Soil depth (cm) 22.5-27.5 | Mobility relative to Termidor SC |
| 12a | 0.19% | S8 | Soprophor 4D384 | 0.062 | 22 | 40 | 28 | 10 | 0 | 0 | 159 * |

* based on a different standard

TABLE 2

| Examples 25-35 Soil mobility studies of formulation concentrates | | | | | | | | | |
|---|---|---|---|---|---|---|---|---|---|
| | % found in segments between . . . cm | | | | | | Rel. | Active ingredient | |
| Ex. No. | 0-2.5 | 2.5-7.5 | 7.5-12.5 | 12.5-17.5 | 17.5-22.5 | 22.5-27.5 | mobility % | content (fipronil) | Composition of the formulation (without active ingredient) |
| V8 | 34 | 51 | 15 | 0 | 0 | 0 | 194 | 96 g/l | Soprophor BSU 200 g/l + Soprophor 4D384 300 g/l + DMSO 300 g/l + γ-butyrolactone ad 1l (system without solubilizer) DC type |
| 25 | 29 | 47 | 23 | 1 | 0 | 0 | 216 | 50 g/l | S2 200 g/l + Soprophor 4D384 300 g/l + DMSO 300 g/l + γ-butyrolactone ad 1l DC type |
| 26 | 18 | 40 | 35 | 6 | 0 | 0 | 263 | 50 g/l | S8 200 g/l + Soprophor 4D384 300 g/l + DMSO 300 g/l + γ-butyrolactone ad 1l SL type |
| 27 | 13 | 37 | 41 | 9 | 0 | 0 | 290 | 50 g/l | S8 400 g/l + Soprophor 4D384 200 g/l + DMSO 250 g/l + γ-butyrolactone ad 1l SL type |
| 28 | 20 | 49 | 30 | 0.26 | 0 | 0 | 236 | 96 g/l | S8 400 g/l + Soprophor 4D384 200 g/l DMSO 250 g/l + γ-butyrolactone ad 1l DC type |
| 29 | 22 | 55 | 24 | 0 | 0 | 0 | 227 | 96 g/l | S8 400 g/l + Soprophor 4D384 300 g/l + DMSO 200 g/l + γ-butyrolactone ad 1l DC type |
| 30 | 14 | 38 | 38 | 10 | 0 | 0 | 287 | 50 g/l | S9 400 g/l + Soprophor 4D384 300 g/l + DMSO 200 g/l + γ-butyrolactone ad 1l SL type |
| 31 | 19 | 40 | 39 | 2 | 0 | 0 | 258 | 96 g/l | S9 400 g/l + Soprophor 4D384 300 g/l + DMSO 200 g/l + γ-butyrolactone ad 1l DC type |

TABLE 2-continued

Examples 25-35 Soil mobility studies of formulation concentrates

| Ex. No. | % found in segments between . . . cm 0-2.5 | 2.5-7.5 | 7.5-12.5 | 12.5-17.5 | 17.5-22.5 | 22.5-27.5 | Rel. mobility % | Active ingredient content (fipronil) | Composition of the formulation (without active ingredient) |
|---|---|---|---|---|---|---|---|---|---|
| 32 | 20 | 43 | 35 | 1 | 0 | 0 | 245 | 96 g/l | S9 200 g/l + Soprophor 4D384 300 g/l + DMSO 300 g/l + γ-butyrolactone ad 1l DC type |
| 33 | 20 | 43 | 36 | 1 | 0 | 0 | 249 | 96 g/l | S9 300 g/l + Soprophor 4D384 300 g/l + DMSO 250 g/l + γ-butyrolactone ad 1l DC type |
| 34 | 61 | 33 | 6 | 1 | 0 | 0 | 146 | 96 g/l | S8 200 g/l + Soprophor 4D384 0 g/l + DMSO 250 g/l + γ-butyrolactone ad 1l DC type |
| 35 | 47 | 41 | 9 | 3 | 0 | 0 | 175 | 96 g/l | S8 400 g/l + Soprophor 4D384 0 g/l + DMSO 250 g/l + γ-butyrolactone ad 1l SL type |
| V9 | 66 | 34 | 10 | 0 | 0 | 0 | 161 | 96 g/l | Soprophor 4D384 400 g/l + DMSO 250 g/l + γ-butyrolactone ad 1l DC type |
| 36 | 14 | 40 | 31 | 15 | 0 | 0 | 176* | 96 g/l | S8 250 g/l + Suprophor 4D384 60 g/l SC type |
| 37 | 12 | 37 | 37 | 14 | 0 | 0 | 182* | 96/l | S8 220 g/l + Soprophor 4D384 80 g/l SC type |

*based on a different standard

TABLE 2a

Examples 38-39 Soil mobility (1250 ppm Fipronil applied)

| Ex. No. | % found in segments between . . . cm 0-2.5 | 2.5-7.5 | 7.5-12.5 | 12.5-17.5 | 17.5-22.5 | 22.5-27.5 | Rel. mobility % | Active ingredient content (fipronil) | Composition of the formulation (without active ingredient) |
|---|---|---|---|---|---|---|---|---|---|
| 38 | 10 | 29 | 32 | 27 | 2 | 0 | 208* | 96 g/l* | S8 250 g/l + Suprophor 4D384 60 g/l SC type |
| 39 | 10 | 28 | 31 | 30 | 1 | 0 | 211* | 96 g/l | S8 220 g/l + Soprophor 4D384 80 g/l SC type |

*based on a different standard

TABLE 3

Examples 40-42 Soil mobilitystudies of SC concentrates with Li 10 soil

| Ex. No. | % found in segments between . . . cm 0-2.5 | 2.5-7.5 | 7.5-12.5 | 12.5-17.5 | 17.5-22.5 | 22.5-27.5 | Rel. mobility % | Active ingredient content (fipronil) | Composition of the formulation (without active ingredient) |
|---|---|---|---|---|---|---|---|---|---|
| 40 | 3 | 11 | 18 | 21 | 26 | 20 | 161 | 96 g/l | SC formulation |
| 41 | 4 | 12 | 15 | 20 | 28 | 22 | 163 | 96 g/l | SC formulation |
| 42 | 4 | 11 | 17 | 22 | 23 | 23 | 162 | 96 g/l | SC formulation |
| V10 | 17 | 31 | 23 | 15 | 9 | 5 | 103 | 96 g/l | Termidor SC |
| V11 | 16 | 35 | 23 | 15 | 8 | 3 | 98 | 96 g/l | Termidor SC |
| V12 | 16 | 35 | 22 | 15 | 8 | 5 | 100 | 96 g/l | Termidor SC |

(Clay 6%, silt 13%, sand 81%, org. L 0.9%, pH 5.9 [$CaCl_2$], max WHC: 24.2 g/100 g)
(625 ppm of Fipronil applied)
SC-formulation of example 39

The examples demonstrate that addition of inventive solubilizers, especially in concentrations greater than the active ingredient concentration, causes a significant increase in the soil mobility, which can be improved a little further by adjuvants. The improved soil mobility occurs both in tank-mix systems (Ex. 9-24) and in ready-to-use formulations (Ex. 25-35) which comprise an inventive polymeric solubilizer.

The invention claimed is:

1. A method for improving the soil mobility of a sparingly soluble insecticide, wherein a combination of the insecticide, a polymeric solubilizer, and an adjuvant, in an aqueous application form is applied to the soil to be treated, wherein the polymeric solubilizer has the property that the active insecticidal ingredient in a 1% by weight aqueous solution of the polymeric solubilizer at 25° C. and 1.01325 bar has a solubility at least forty times higher than under the same conditions in pure water, and wherein the weight ratio of active ingredient to solubilizer is ≤1, and wherein the solubilizer is selected from groups A1, B1, D and combinations thereof:

A1. hyperbranched polycarbonates in which the hyperbranched polycarbonate is bonded to at least one linear or comb-type polymer and/or at least one functional $C_1$-$C_{24}$ unit comprising a carboxylic acid group, a sulfonic acid group, a sulfenic acid group, a sulfinic acid group, a sulfuric ester group, a phosphonic acid group, an amino group or at least two hydroxyl-$C_2$-$C_{10}$-alkyl groups;

B1. vinyllactam copolymers obtained from

B1-1. 60-99% by weight (based on the overall copolymer) of 5-7-membered 1-vinyl-2-lactam and B1-2. 1 to 40% by weight of at least one monomer selected from the group of the B1-21 $C_8$-$C_{30}$-alkyl esters of monoethylenically unsaturated $C_3$-$C_8$-carboxylic acids, wherein the percentages by weight of the individual components add up to 100% by weight;

D. copolymers based on ethylenically unsaturated dicarboxylic mono- and diesters, obtained from D1 at least one monomer from the group of olefins, vinyl ethers and styrene and D2 at least one monomer from the group of mono- and diesters of ethylenically unsaturated dicarboxylic acids, wherein the alcohol group of the ester has a structure of the formula (V)

$$—(R^{10}—O)_n—(R^{11}—O)_p—R^{12} \quad (V)$$

wherein:

$R^{10}$ is 1,2-propylene or 2,3-propylene;

$R^{11}$ is ethylene;

$R^{12}$ is H, unbranched or branched $C_1$-$C_{40}$-alkyl, phenyl, phenyl substituted by $C_1$-$C_{20}$-alkyl, benzyl, benzyl substituted by $C_1$-$C_{20}$-alkyl;

n is an integer from 0 to 140 and p is an integer from 0 to 100, wherein the sum of n and p is at least 1, wherein the insecticide is selected from the group consisting of fipronil, allethrin, alpha-cypermethrin, beta-cyfluthrin, bifenthrin, bioallethrin, 4-chloro-2-(2-chloro-2-methylpropyl)-5[(6-iodo-3 -pyridinyl) methoxyl]-3 (2H)-pyridazinone (CAS-RN: 120955-77-3), chlorantraniliprole, chlorfenapyr, chlorpyrifos, cyantraniliprole, cyfluthrin, cyhalothrin, cypermethrin, deltamethrin, etofenprox, fenoxycarb, flufenoxuron, hydramethylnon, imidacloprid, indoxacarb, metaflumizone, permethrin, pyriproxifen, tebufenozide and tralomethrin.

2. The method according to claim 1, wherein the insecticide is fipronil.

3. The method according to claim 1, wherein the solubilizer is selected from group A1.

4. The method according to claim 1, wherein the solubilizer is selected from group B1.

5. The method according to claim 1, wherein the solubilizer is selected from group D.

6. The method according to claim 1, wherein a mixture of two or more polymeric solubilizers is used.

7. The method according to claim 1, wherein the weight ratio of active ingredient(s) and solubilizer(s) is from 1:1 to 1:200.

8. The method according to claim 1, wherein the combination of the insecticide and a polymeric solubilizerfurther comprises one or more adjuvants selected from the group consisting of:

Z1 tristyrylalkyl ether sulfates or phosphates;

Z2 nonionic surfactants based on perfluoroalkyl ethoxylate

Z3 a mixture of 83% highly refined petroleum oil based on paraffin and 17% alkylarylpolyoxyethylene glycols;

Z4 polyethers or organomodified tri- and polysiloxanes;

Z5 a nonionic surfactant mixture of alkyloxypolyethyleneoxyethanols of the formula $CH_3CH[(CH_2)_nCH_3][O(C_2H_4O)_mH]$where n=9-15 and m=3-40;

Z6 a silicone surfactant mixture of 100% 2-(3-hydroxypropyl)heptamethyltrisiloxane, ethoxylated acetate, allyloxypolyethylene glycol monoallylacetate and polyethylene glycol diacetate;

Z7 a biodegradable, low-foaming nonionic surfactant comprising primary alkyl polyoxyethylene ethers, free fatty acids and adjuvants;

Z8 a nonionic surfactant mixture of fatty acid and alcohol ethoxylates based on soybeans;

Z9 an anionic surfactant mixture comprising 58% ammonium n-alcohol ether sulfate;

Z10 an anionic surfactant mixture comprising 58% ammonium nonylphenol ether sulfate;

Z11 a mixture of polyalkylene oxide-modified polydimethylsiloxane and nonionic surfactants;

Z12 a nonionic detergent composed of 100% polyoxyethylene (10)-isooctyl cyclohexyl ether;

Z13 alkoxylated fatty alcohols and/or fatty acids, which may additionally each be etherified, sulfonated or phosphonated; and combinations thereof.

9. A method for controlling soil-dwelling invertebrate pests, wherein a) at least one sparingly soluble active insecticidal ingredient selected from the group consisting of fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)-pyridazinone (CAS-RN: 120955-77-3), chlorantraniliprole, chlorfenapyr, chlorpyrifos, cyantraniliprole, cyfluthrin, cyhalothrin, cypermethrin, deltamethrin, etofenprox, fenoxycarb, flufenoxuron, hydramethylnon, imidacloprid, indoxacarb, metaflumizone, permethrin, pyriproxifen, tebufenozide, and tralomethrin; and b) at least one polymeric solubilizer which has the property that the active termiticidal ingredient in a 1% by weight aqueous solution of the polymeric solubilizer at 25° C. and 1.01325 bar has a solubility at least forty times higher than under the same conditions in pure water, and is selected from the group of the solubilizers A1 and B1:

A1. hyperbranched polycarbonates in which the hyperbranched polycarbonate is bonded to at least one linear or comb-type polymer and/or at least one functional $C_1$-$C_{24}$ unit comprising a carboxylic acid group, a sulfonic acid group, a sulfenic acid group, a sulfinic acid group, a sulfuric ester group, a phosphonic acid group, an amino group or at least two hydroxyl groups;

B1. vinyllactam copolymers obtained from

B1-1. 60-99% by weight (based on the overall copolymer) of 5-7-membered 1-vinyl-2-lactam and B1-2. 1 to 40% by weight of at least one monomer selected from the group of the B1-21 $C_8$-$C_{30}$-alkyl esters of monoethylenically unsaturated $C_3$-$C_8$-carboxylic acids, wherein the percentages by weight of the individual components add up to 100% by weight, in a weight ratio (a:b) ≤1 in an aqueous application form are applied to or into a soil used by the pests.

10. The method according to claim 9, wherein the pests are ants and/or are present on the soil of a sugarbeet crop.

11. The method according to claim 9, wherein the pests are termites, and wherein the insecticidal active ingredient is a termiticide.

12. The method according to claim 11, wherein the soil is present under a building or within a radius of 10 m thereof.

13. The method according to claim 11, wherein the termiticide is applied in trenches with a depth of 1-3 inches.

14. The method according to claim 11, wherein the concentration of the termiticide in the aqueous application form is at least 1000 ppm.

15. The method according to claim 9, wherein the insectididal active ingredient is fipronil.

16. The method according to claim 9, wherein the polymeric solubilizer is A1.

17. The method according to claim 9, wherein the sparingly soluble active insecticidal ingredient, the polymeric solubilizer and if appropriate one or more adjuvants are used as the formulation.

18. The method according to claim 9, wherein the polymeric solubilizer and/or one or more adjuvants are added as a tank mix to the aqueous application form.

* * * * *